(12) United States Patent
Lim et al.

(10) Patent No.: US 7,790,739 B2
(45) Date of Patent: Sep. 7, 2010

(54) TYROSINE KINASE INHIBITORS

(75) Inventors: Jongwon Lim, Lexington, MA (US); Ana Esther Gabarda Ortega, Madrid (ES)

(73) Assignee: Merck & Co., Inc. and Merck Sharp & Dohme Corp., Rahway, NJ (US)

( * ) Notice: Subject to any disclaimer, the term of this patent is extended or adjusted under 35 U.S.C. 154(b) by 52 days.

(21) Appl. No.: 12/083,745

(22) PCT Filed: Oct. 18, 2006

(86) PCT No.: PCT/US2006/040664
§ 371 (c)(1),
(2), (4) Date: Apr. 17, 2008

(87) PCT Pub. No.: WO2007/050380
PCT Pub. Date: May 3, 2007

(65) Prior Publication Data
US 2009/0247565 A1 Oct. 1, 2009

Related U.S. Application Data

(60) Provisional application No. 60/728,997, filed on Oct. 21, 2005.

(51) Int. Cl.
*A61K 31/44* (2006.01)
*C07D 455/04* (2006.01)
*C07D 413/00* (2006.01)
(52) U.S. Cl. .................. 514/290; 546/80; 548/126
(58) Field of Classification Search .............. 546/80; 514/290, 126; 548/126, 290
See application file for complete search history.

(56) References Cited

U.S. PATENT DOCUMENTS

| 5,726,325 A | 3/1998 | Yoshida et al. |
| 2003/0114432 A1 | 6/2003 | Clare et al. |

FOREIGN PATENT DOCUMENTS

| WO | WO 88/03138 | 5/1988 |
| WO | WO 03/084931 | 10/2003 |
| WO | WO 2007/002254 | 1/2007 |
| WO | WO 2007/050383 | 5/2007 |
| WO | WO 2007/050401 | 5/2007 |

OTHER PUBLICATIONS

Bollinger et al., "Benzo[4,5]cycloheptal . . . ", Helvetica Chimica Acta, vol. 73 (1990).*
Pinedo et al., "Translational Research . . . ", The Oncologist 2000,, 5 (suppl1): 1-2 (www.The Oncologist.com).*
McMahon, Gerald, "VEGF Receptor Signaling in Tumor Angiogenesis", The Oncologist 2000; 5(suppl 1): 3-10 (www.The Oncologist.com).*
Trusolino, L et al., Nature Reviews: Cancer, vol. 2, pp. 289-300 (2002), "Scatter-factor semaphorin receptors: cell signalling for invasive growth".
Ma, PC et al. Cancer Research, vol. 65, No. 4, pp. 1479-1488 (2005), "Functional expression and mutations of c-Met and its therapeutic inhibition with SU11274 and small interfering RNA in non-small cell lung cancer".
Ma, PC et al. Cancer Research, vol. 63, pp. 6272-6281 (2003), "c-MET mutational analysis in small cell lung cancer: novel juxtamembrane domain mutations regulating cytoskeletal functions".
Christensen, JG et al., Cancer Research., vol. 63, pp. 7345-7355 (2003), "A selective small molecule inhibitor of c-Met kinase inhibits c-Met-dependent phenotypes in vitro and exhibits cytoreductive antitumor activity in vivo".
Sattler, M et al., Cancer Research, vol. 63, pp. 5462-5469 (2003), "A novel small molecule Met inhibitor induces apoptosis in cells transformed by the oncogenic TPR-MET tyrosine kinase".
Christensen, JG et al., Cancer Letters, vol. 225, pp. 1-26 (2005), "c-Met as a target for human cancer and characterization of inhibitors for therapeutic intervention".
Dermer, GB, Bio/technology, vol. 12, pp. 320 (1994), "Another anniversary for the war on cancer".
Freshney, R, Culture of Animal Cells, pp. 1-6 (1983).
Puri, N et al., Cancer Research, vol. 67, No. 8, pp. 3529-3534 (2007), "A selective small molecule inhibitor of c-Met, PHA665752, inhibits tumorigenicity and angiogenesis in mouse lung cancer xenografts".
Zou, HY et al., Cancer Research, vol. 67, No. 9, pp. 4408-4417 (2007), "An orally available small-molecule inhibitor of c-Met, PF-2341066, exhibits cytoreductive antitumor efficacy through antiproliferative and antiangiogenic mechanisms".
Cassinelli, G et al., Molecular Cancer Therapeutics, vol. 5, No. 9, pp. 2388-2397 (2006), "Inhibition of c-Met and prevention of spontaneous metastatic spreading by the 2-indolinone RPI-1".
Martens, T et al., Clinical Cancer Research, vol. 12, No. 20, pp. 6144-6152 (2006), "A novel one-armed anti-c-Met antibody inhibits glioblastoma growth in vivo".
Ross, R et al., Poster B249, 2007 AARC-NCI-EORTC International Conference on Molecular Targets and Cancer Therapeutics, Oct. 2007, "A Phase 2 Study of the Dual MET/VEGFR2 Inhibitor XL880 in Patients (pts) with Papillary Renal Carcinoma (PRC)".
Office Communication from the USPTO mailed Apr. 28, 2008 with a three-month reply due of Jul. 28, 2008.
Amendment and Response dated Jun. 4, 2008 in reply to the Office Action mailed Apr. 28, 2008 from the USPTO.

* cited by examiner

*Primary Examiner*—James O. Wilson
*Assistant Examiner*—Paul V. Ward
(74) *Attorney, Agent, or Firm*—David A. Muthard

(57) ABSTRACT

The present invention relates to imidazo[1,2-a]pyrimidine derivatives, that are useful for treating cellular proliferative diseases, for treating disorders associated with MET activity, and for inhibiting the receptor tyrosine kinase MET. The invention also related to compositions which comprise these compounds, and methods of using them to treat cancer in mammals.

6 Claims, No Drawings

SEQUENCE LISTING

```
<160> NUMBER OF SEQ ID NOS: 1

<210> SEQ ID NO 1
<211> LENGTH: 15
<212> TYPE: PRT
<213> ORGANISM: Artificial Sequence
<220> FEATURE:
<223> OTHER INFORMATION: Completely Synthetic Amino Acid Sequence

<400> SEQUENCE: 1

Glu Gln Glu Asp Glu Pro Glu Gly Asp Tyr Phe Glu Trp Leu Glu
1               5                   10                  15
```

TYROSINE KINASE INHIBITORS

PRIORITY CLAIM

This application is a §371 application of PCT/US2006/040664 that was filed on Oct. 18, 2006, which claims priority from the U.S. Provisional Application No. 60/728,997, filed on Oct. 21, 2005, now expired.

BACKGROUND OF THE INVENTION

This invention relates to fused tricyclic cyclohepta[1,2-5b]pyridine compounds and related compounds that are inhibitors of tyrosine kinases, in particular the receptor tyrosine kinase MET, and are useful in the treatment of cellular proliferative diseases, for example cancer, hyperplasias, restenosis, cardiac hypertrophy, immune disorders and inflammation.

Studies on signal transduction pathways have generated various promising molecular targets for therapeutic inhibition in cancer therapy. Receptor tyrosine kinases (RTK) represent an important class of such therapeutic targets. Recently, members of the MET proto-oncogene family, a subfamily of receptortyrosine kinases, have drawn special attention to the association between invasion and metastasis. The MET family, including MET (also referred to as c-Met) and RON receptors, can function as oncogenes like most tyrosine kinases. MET has been shown to be overexpressed and/or mutated in a variety of malignancies. A number of MET activating mutations, many of which are located in the tyrosine kinase domain, have been detected in various solid tumors and have been implicated in invasion and metastasis of tumor cells.

The c-Met proto-oncogene encodes the MET receptor tyrosine kinase. The MET receptor is a 190 kDa glycosylated dimeric complex composed of a 50 kDa alpha chain disulfide-linked to a 145 kDa beta chain. The alpha chain is found extracellularly while the beta chain contains extracellular, transmembrane and cytosolic domains. MET is synthesized as a precursor and is proteolytically cleaved to yield mature alpha and beta subunits. It displays structural similarities to semaphoring and plexins, a ligand-receptor family that is involved in cell-cell interaction.

The natural ligand for MET is hepatocyte growth factor (HGF), a disulfide linked heterodimeric member of the scatter factor family that is produced predominantly by mesenchymal cells and acts primarily on MET-expressing epithelial and endothelial cells in an endocrine and/or paraendocrine fashion. HGF has some homology to plasminogen.

It is known that stimulation of MET via hepatocyte growth factor (also known as scatter factor, HGF/SF) results in a plethora of biological and biochemical effects in the cell. Activation of c-Met signaling can lead to a wide array of cellular responses including proliferation, survival, angiogenesis, wound healing, tissue regeneration, scattering, motility, invasion and branching morphogenesis. HGF/MET signaling also plays a major role in the invasive growth that is found in most tissues, including cartilage, bone, blood vessels, and neurons.

Various c-Met mutations have been well described in multiple solid tumors and some hematologic malignancies. The prototypic c-Met mutation examples are seen in hereditary and sporadic human papillary renal carcinoma (Schmidt, L. et al., *Nat. Tenet.* 1997, 16, 68-73; Jeffers, M. et al., *Proc. Nat. Acad. Sci.* 1997, 94, 11445-11500). Other reported examples of c-Met mutations include ovarian cancer, childhood hepatocellular carcinoma, metastatic head and neck squamous cell carcinomas and gastric cancers. HGF/MET has been shown to inhibit anoikis, suspension-induced programmed cell death (apoptosis), in head and neck squamous cell carcinoma cells.

MET signaling is implicated in various cancers, especially renal. The nexus between MET and colorectal cancer has also been established. Analysis of c-Met expression during colorectal cancer progression showed that 50% of the carcinoma specimens analyzed expressed 5-50-fold higher levels of MET mRNA transcripts and protein versus the adjacent normal colonic mucosa. In addition, when compared to the primary tumor, 70% of colorectal cancer liver metastasis showed MET overexpression.

MET is also implicated in glioblastoma. High-grade malignant gliomas are the most common cancers of the central nervous system. Despite treatment with surgical resection, radiation therapy, and chemotherapy, the mean overall survival is <1.5 years, and few patients survive for >3 years. Human malignant gliomas frequently express both HGF and MET, which can establish an autocrine loop of biological significance. Glioma MET expression correlates with glioma grade, and an analysis of human tumor specimens showed that malignant gliomas have a 7-fold higher HGF content than low-grade gliomas. Multiple studies have demonstrated that human gliomas frequently co-express HGF and MET and that high levels of expression are associated with malignant progression. It was further shown that HGF-MET is able to activate Akt and protect glioma cell lines from apoptotic death, both in vitro and in vivo.

RON shares a similar structure, biochemical features, and biological properties with MET. Studies have shown RON overexpression in a significant fraction of breast carcinomas and colorectal adenocarcinomas, but not in normal breast epithelia or benign lesions. Cross-linking experiments have shown that RON and MET form a non-covalent complex on the cell surface and cooperate in intracellular signaling. RON and MET genes are significantly co-expressed in ovarian cancer cell motility and invasiveness. This suggests that co-expression of these two related receptors might confer a selective advantage to ovarian carcinoma cells during either tumor onset or progression.

A number of reviews on MET and its function as an oncogene have recently been published: *Cancer and Metastasis Review* 22:309-325 (2003); *Nature Reviews/Molecular Cell Biology* 4:915-925 (2003); *Nature Reviews/Cancer* 2:289-300 (2002).

Since dysregulation of the HGF/MET signaling has been implicated as a factor in tumorgenesis and disease progression in many tumors, different strategies for therapeutic inhibition of this important RTK molecule should be investigated. Specific small molecule inhibitors against HGF/MET signaling and against RON/MET signaling have important therapeutic value for the treatment of cancers in which Met activity contributes to the invasive/metastatic phenotype.

SUMMARY OF THE INVENTION

The present invention relates to 5H-benzo[4,5]cyclohepta[1,2-b]pyridine derivatives, that are useful for treating cellular proliferative diseases, for treating disorders associated with MET activity, and for inhibiting the receptor tyrosine kinase MET. The compounds of the invention may be illustrated by the Formula I:

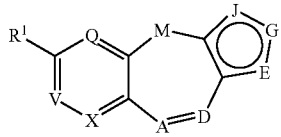

DETAILED DESCRIPTION OF THE INVENTION

The compounds of this invention are useful in the inhibition of tyrosine kinases, in particular the receptor tyrosine kinase MET, and are illustrated by a compound of Formula I:

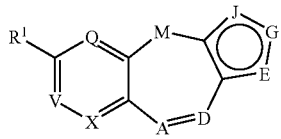

I or pharmaceutically acceptable salts or stereoisomers thereof, wherein:

A and D are independently selected from —NR$^{10}$— and —CR$^4$R$^5$—, provided that if A is —NR$^{10}$—, then D is —CR$^4$R$^5$—; and if D is —NR$^{10}$—, then A is —CR$^4$R$^5$—;

E, G and J are independently selected from: O, S, —NR$^{10}$— and —CR$^6$—, provided at least one of E, G and J are not —CR$^6$—, M is selected from: —CR$^2$R$^3$—, —C(═O)—, —C(═N—OR$^c$)—, —NR$^{10}$C(═O)— and —C(═O)NR$^{10}$—;

Q, V and X are independently selected from: N and —CR$^8$—;

a dashed line represents an optional double bond;

a is independently 0 or 1;

b is independently 0 or 1;

m is independently 0, 1, or 2;

R$^1$ is selected from halogen, aryl, heterocyclic, C$_{1-6}$alkyl, —O—C$_{1-6}$alkyl and NR$^{10}$R$^{11}$; said alkyl, aryl and heterocyclic group optionally substituted with one to five substituents, each substituent independently selected from R$^8$;

R$^2$ and R$^3$ are independently selected from hydrogen, OH, —O—C$_{1-6}$ alkyl, —O—C(═O)C$_{1-6}$ alkyl, —O-aryl and NR$^{10}$R$^{11}$, each alkyl and aryl optionally substituted with one to five substituents, each substituent independently selected from R$^8$;

R$^4$ and R$^5$ are each independently selected from hydrogen, C$_{1-6}$alkyl, OH, —O—C$_{1-6}$alkyl, —O—C(═O)C$_{1-6}$ alkyl, —O-aryl, S(O)$_m$R$^a$ and NR$^{10}$R$^{11}$, each alkyl and aryl optionally substituted with one to five substituents, each substituent independently selected from R$^8$;

R$^6$ is selected from hydrogen, C$_{1-6}$alkyl, C$_{2-6}$ alkenyl, C$_{2-6}$ alkynyl, OH, —O—C$_{1-6}$alkyl, —O—C(═O)C$_{1-6}$ alkyl, —O-aryl, S(O)$_m$R$^a$, —C(═O)NR$^{10}$R$^{11}$, —NHS(O)$_2$NR$^{10}$R$^{11}$ and NR$^{10}$R$^{11}$, each alkyl, alkenyl, alkynyl and aryl optionally substituted with one to five substituents, each substituent independently selected from R$^{18}$;

R$^8$ independently is:
1) (C═O)$_a$O$_b$C$_1$-C$_{10}$ alkyl,
2) (C═O)$_a$O$_b$aryl,
3) C$_2$-C$_{10}$ alkenyl,
4) C$_2$-C$_{10}$ alkynyl,
5) (C═O)$_a$O$_b$ heterocyclyl,
6) CO$_2$H,
7) halo,
8) CN,
9) OH,
10) O$_b$C$_1$-C$_6$ perfluoroalkyl,
11) O$_a$(C═O)$_b$NR$^{10}$R$^{11}$,
12) S(O)$_m$R$^a$,
13) S(O)$_2$NR$^{10}$R$^{11}$,
14) OS(═O)R$^a$,
15) oxo,
16) CHO,
17) (N═O)R$^{10}$R$^{11}$,
18) (C═O)$_a$O$_b$C$_3$-C$_8$ cycloalkyl,
19) O$_b$SiR$^a_3$, or
20) NO$_2$;

said alkyl, aryl, alkenyl, alkynyl, heterocyclyl, and cycloalkyl optionally substituted with one, two or three substituents selected from R$^9$;

two R$^8$s, attached to the same carbon atom are combined to form —(CH$_2$)$_u$— wherein u is 3 to 6 and one or two of the carbon atoms is optionally replaced by a moiety selected from O, S(O)$_m$, —N(R$^a$)C(O)—, —N(R$^b$)— and —N(COR$^a$)—;

R$^9$ is independently selected from:
1) (C═O)$_a$O$_b$(C$_1$-C$_{10}$)alkyl,
2) O$_b$(C$_1$-C$_3$)perfluoroalkyl,
3) oxo,
4) OH,
5) halo,
6) CN,
7) (C$_2$-C$_{10}$)alkenyl,
8) (C$_2$-C$_{10}$)alkynyl,
9) (C═O)$_a$O$_b$(C$_3$-C$_6$)cycloalkyl,
10) (C═O)$_a$O$_b$(C$_0$-C$_6$)alkylene-aryl,
11) (C═O)$_a$O$_b$(C$_0$-C$_6$)alkylene-heterocyclyl,
12) (C═O)$_a$O$_b$(C$_0$-C$_6$)alkylene-N(R$^b$)$_2$,
13) C(O)R$^a$,
14) (C$_0$-C$_6$)alkylene-CO$_2$R$^a$,
15) C(O)H,
16) (C$_0$-C$_6$)alkylene-CO$_2$H,
17) C(O)N(R$^b$)$_2$,
18) S(O)$_m$R$^a$, and
19) S(O)$_2$NR$^{10}$R$^{11}$;

said alkyl, alkenyl, alkynyl, cycloalkyl, aryl, and heterocyclyl is optionally substituted with one, two or three substituents selected from R$^b$, OH, (C$_1$-C$_6$)alkoxy, halogen, CO$_2$H, CN, O(C═O)C$_1$-C$_6$ alkyl, oxo, and N(R$^b$)$_2$; or two R$^9$s, attached to the same carbon atom are combined to form —(CH$_2$)$_u$— wherein u is 3 to 6 and one or two of the carbon atoms is optionally replaced by a moiety selected from O, S(O)$_m$, —N(R$^a$)C(O)—, —N(R$^b$)— and —N(COR$^a$)—;

R$^{10}$ and R$^{11}$ are independently selected from:
1) H,
2) (C═O)O$_b$C$_1$-C$_{10}$ alkyl,
3) (C═O)O$_b$C$_3$-C$_8$ cycloalkyl,
4) (C═O)O$_b$aryl,
5) (C═O)O$_b$heterocyclyl,
6) C$_1$-C$_{10}$ alkyl,
7) aryl, 8) $C_2$-$C_{10}$ alkenyl,
9) $C_2$-$C_{10}$ alkynyl,
10) heterocyclyl,
11) $C_3$-$C_8$ cycloalkyl,
12) $SO_2R^a$, and
13) $(C=O)NR^b{}_2$, said alkyl, cycloalkyl, aryl, heterocylyl, alkenyl, and alkynyl is optionally substituted with one, two or three substituents selected from $R^8$, or $R^{10}$ and $R^{11}$ can be taken together with the nitrogen to which they are attached to form a monocyclic or bicyclic heterocycle with 5-7 members in each ring and optionally containing, in addition to the nitrogen, one or two additional heteroatoms selected from N, O and S, said monocyclic or bicyclic heterocycle optionally substituted with one, two or three substituents selected from $R^9$;

$R^a$ is independently selected from: $(C_1$-$C_6)$alkyl, $(C_2$-$C_6)$alkenyl, $(C_3$-$C_6)$cycloalkyl, aryl, —$(C_1$-$C_6)$alkylenearyl, heterocyclyl and —$(C_1$-$C_6)$alkyleneheterocyclyl;

$R^b$ is independently selected from: H, $(C_1$-$C_6)$alkyl, aryl, —$(C_1$-$C_6)$alkylenearyl, heterocyclyl, —$(C_1$-$C_6)$alkyleneheterocyclyl, $(C_3$-$C_6)$cycloalkyl, $(C=O)OC_1$-$C_6$ alkyl, $(C=O)C_1$-$C_6$ alkyl or $S(O)_2R^a$; and $R^c$ is independently selected from: H, $(C_1$-$C_6)$alkyl, $(C_2$-$C_6)$alkenyl, $(C_3$-$C_6)$cycloalkyl, aryl, —$(C_1$-$C_6)$alkylenearyl, heterocyclyl and —$(C_1$-$C_6)$alkyleneheterocyclyl.

Another embodiment of the present invention is illustrated by a compound of Formula II:

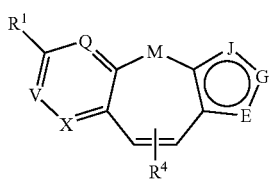

II or pharmaceutically acceptable salts or stereoisomers thereof, wherein:

E, G and J are independently selected from: S, O, —$NR^{10}$— and —$CR^6$—; provided at least one of E, G and J are not —$CR^6$—, M is selected from: —$CR^2R^3$—, —$C(=O)$— and —$C(=N-OR^c)$—;

Q, V and X are independently selected from: N and —$CR^8$—;

a dashed line represents an optional double bond;

a is independently 0 or 1;

b is independently 0 or 1;

m is independently 0, 1, or 2;

$R^1$ is selected from halogen, aryl, heterocyclic, —O—$C_{1-6}$ alkyl and $NR^{10}R^{11}$; said alkyl, aryl and heterocyclic group optionally substituted with one to five substituents, each substituent independently selected from $R^8$;

$R^2$ and $R^3$ are independently selected from hydrogen, OH, —O—$C_{1-6}$ alkyl, —O—$C(=O)C_{1-6}$ alkyl, —O-aryl and $NR^{10}R^{11}$, each alkyl and aryl optionally substituted with one to five substituents, each substituent independently selected from $R^8$;

$R^4$ is selected from: hydrogen, $C_{1-6}$alkyl, OH, $NO_2$, —O—$C_{1-6}$alkyl, —O—$C(=O)C_{1-6}$ alkyl, —O-aryl, $S(O)_m R^a$ and $NR^{10}R^{11}$, each alkyl and aryl optionally substituted with one to five substituents, each substituent independently selected from $R^8$;

$R^6$ is selected from hydrogen, $C_{1-6}$alkyl, $C_{2-6}$ alkenyl, $C_{2-6}$ alkynyl, OH, —O—$C_{1-6}$alkyl, —O—$C(=O)C_{1-6}$ alkyl, —O-aryl, $S(O)_m R^a$, —$C(=O)NR^{10}R^{11}$, —$NHS(O)_2 NR^{10}R^{11}$ and $NR^{10}R^{11}$, each alkyl, alkenyl, alkynyl and aryl optionally substituted with one to five substituents, each substituent independently selected from $R^8$;

$R^8$ independently is:
1) $(C=O)_a O_b C_1$-$C_{10}$ alkyl,
2) $(C=O)_a O_b$ aryl,
3) $C_2$-$C_{10}$ alkenyl,
4) $C_2$-$C_{10}$ alkynyl,
5) $(C=O)_a O_b$ heterocyclyl,
6) $CO_2H$,
7) halo,
8) CN,
9) OH,
10) $O_b C_1$-$C_6$ perfluoroalkyl,
11) $O_a(C=O)_b NR^{10}R^{11}$,
12) $S(O)_m R^a$,
13) $S(O)_2 NR^{10}R^{11}$,
14) $OS(=O)R^a$,
15) oxo,
16) CHO,
17) $(N=O)R^{10}R^{11}$,
18) $(C=O)_a O_b C_3$-$C_8$ cycloalkyl,
19) $O_b SiR^a{}_3$, or
20) $NO_2$;

said alkyl, aryl, alkenyl, alkynyl, heterocyclyl, and cycloalkyl optionally substituted with one, two or three substituents selected from $R^9$;

two $R^8$s, attached to the same carbon atom are combined to form —$(CH_2)_u$— wherein u is 3 to 6 and one or two of the carbon atoms is optionally replaced by a moiety selected from O, $S(O)_m$, —$N(R^a)C(O)$—, —$N(R^b)$— and —$N(COR^a)$—;

$R^9$ is independently selected from:
1) $(C=O)_a O_b (C_1$-$C_{10})$alkyl,
2) $O_b(C_1$-$C_3)$perfluoroalkyl,
3) oxo,
4) OH,
5) halo,
6) CN,
7) $(C_2$-$C_{10})$alkenyl,
8) $(C_2$-$C_{10})$alkynyl,
9) $(C=O)_a O_b (C_3$-$C_6)$cycloalkyl,
10) $(C=O)_a O_b (C_0$-$C_6)$alkylene-aryl,
11) $(C=O)_a O_b (C_0$-$C_6)$alkylene-heterocyclyl,
12) $(C=O)_a O_b (C_0$-$C_6)$alkylene-$N(R^b)_2$,
13) $C(O)R^a$,
14) $(C_0$-$C_6)$alkylene-$CO_2 R^a$,
15) $C(O)H$,
16) $(C_0$-$C_6)$alkylene-$CO_2 H$,
17) $C(O)N(R^b)_2$,
18) $S(O)_m R^a$, and
19) $S(O)_2 NR^{10}R^{11}$;

said alkyl, alkenyl, alkynyl, cycloalkyl, aryl, and heterocyclyl is optionally substituted with one, two or three substituents selected from $R^b$, OH, $(C_1$-$C_6)$alkoxy, halogen, $CO_2H$, CN, $O(C=O)C_1$-$C_6$ alkyl, oxo, and $N(R^b)_2$; or two $R^9$s, attached to the same carbon atom are combined to form —$(CH_2)_u$— wherein u is 3 to 6 and one or two of the carbon atoms is optionally replaced by a moiety selected from O, $S(O)_m$, —$N(R^a)C(O)$—, —$N(R^b)$— and —$N(COR^a)$—;

$R^{10}$ and $R^{11}$ are independently selected from:
1) H,
2) $(C=O)O_bC_1$-$C_{10}$ alkyl,
3) $(C=O)O_bC_3$-$C_8$ cycloalkyl,
4) $(C=O)O_b$aryl,
5) $(C=O)O_b$heterocyclyl,
6) $C_1$-$C_{10}$ alkyl,
7) aryl,
8) $C_2$-$C_{10}$ alkenyl,
9) $C_2$-$C_{10}$ alkynyl,
10) heterocyclyl,
11) $C_3$-$C_8$ cycloalkyl,
12) $SO_2R^a$, and
13) $(C=O)NR^b{}_2$, said alkyl, cycloalkyl, aryl, heterocylyl, alkenyl, and alkynyl is optionally substituted with one, two or three substituents selected from $R^8$, or $R^{10}$ and $R^{11}$ can be taken together with the nitrogen to which they are attached to form a monocyclic or bicyclic heterocycle with 5-7 members in each ring and optionally containing, in addition to the nitrogen, one or two additional heteroatoms selected from N, O and S, said monocyclic or bicyclic heterocycle optionally substituted with one, two or three substituents selected from $R^9$;

$R^a$ is independently selected from: $(C_1$-$C_6)$alkyl, $(C_2$-$C_6)$alkenyl, $(C_3$-$C_6)$cycloalkyl, aryl, —$(C_1$-$C_6)$alkylenearyl, heterocyclyl and —$(C_1$-$C_6)$alkyleneheterocyclyl;

$R^b$ is independently selected from: H, $(C_1$-$C_6)$alkyl, aryl, —$(C_1$-$C_6)$alkylenearyl, heterocyclyl, —$(C_1$-$C_6)$alkyleneheterocyclyl, $(C_3$-$C_6)$cycloalkyl, $(C=O)OC_1$-$C_6$ alkyl, $(C=O)C_1$-$C_6$ alkyl or $S(O)_2R^a$; and $R^c$ is independently selected from: H, $(C_1$-$C_6)$alkyl, $(C_2$-$C_6)$ alkenyl, $(C_3$-$C_6)$cycloalkyl, aryl, —$(C_1$-$C_6)$alkylenearyl, heterocyclyl and —$(C_1$-$C_6)$alkyleneheterocyclyl.

Another embodiment of the present invention is illustrated by a compound of Formula III:

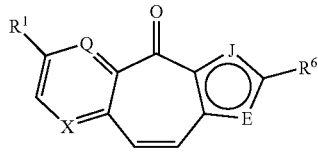

III or pharmaceutically acceptable salts thereof, wherein:

E and J are independently selected from: O, S, —$NR^{10}$— and —$CR^6$—; provided at least one of E and J are not —$CR^6$—, Q is selected from: N and —$CR^8$—;

a is independently 0 or 1;

b is independently 0 or 1;

m is independently 0, 1, or 2;

$R^1$ is selected from halogen, aryl, heterocyclic, and $NR^{10}R^{11}$; said aryl and heterocyclic group optionally substituted with one to five substituents, each substituent independently selected from $R^8$;

$R^6$ is selected from hydrogen, halogen, $C_{1-6}$alkyl, $C_{2-6}$ alkenyl, $C_{2-6}$ alkynyl, OH, —O—$C_{1-6}$alkyl, —O—C(=O) $C_{1-6}$ alkyl, —O-aryl, $S(O)_mR^a$ and $NR^{10}R^{11}$, each alkyl and aryl optionally substituted with one to five substituents, each substituent independently selected from $R^8$;

$R^8$ independently is:
1) $(C=O)_aO_bC_1$-$C_{10}$ alkyl,
2) $(C=O)_aO_b$aryl,
3) $C_2$-$C_{10}$ alkenyl,
4) $C_2$-$C_{10}$ alkynyl,
5) $(C=O)_aO_b$ heterocyclyl,
6) $CO_2H$,
7) halo,
8) CN,
9) OH,
10) $O_bC_1$-$C_6$ perfluoroalkyl,
11) $O_a(C=O)_bNR^{10}R^{11}$,
12) $S(O)_mR^a$,
13) $S(O)_2NR^{10}R^{11}$,
14) $OS(=O)R^a$,
15) oxo,
16) CHO,
17) $(N=O)R^{10}R^{11}$,
18) $(C=O)_aO_bC_3$-$C_8$ cycloalkyl,
19) $O_bSiR^a{}_3$, or
20) $NO_2$;

said alkyl, aryl, alkenyl, alkynyl, heterocyclyl, and cycloalkyl optionally substituted with one, two or three substituents selected from $R^9$;

two $R^8$s, attached to the same carbon atom are combined to form —$(CH_2)_u$— wherein u is 3 to 6 and one or two of the carbon atoms is optionally replaced by a moiety selected from O, $S(O)_m$, —$N(R^a)C(O)$—, —$N(R^b)$— and —$N(COR^a)$—;

$R^9$ is independently selected from:
1) $(C=O)_aO_b(C_1$-$C_{10})$alkyl,
2) $O_b(C_1$-$C_3)$perfluoroalkyl,
3) oxo,
4) OH,
5) halo,
6) CN,
7) $(C_2$-$C_{10})$alkenyl,
8) $(C_2$-$C_{10})$alkynyl,
9) $(C=O)_aO_b(C_3$-$C_6)$cycloalkyl,
10) $(C=O)_aO_b(C_0$-$C_6)$alkylene-aryl,
11) $(C=O)_aO_b(C_0$-$C_6)$alkylene-heterocyclyl,
12) $(C=O)_aO_b(C_0$-$C_6)$alkylene-$N(R^b)_2$,
13) $C(O)R^a$,
14) $(C_0$-$C_6)$alkylene-$CO_2R^a$,
15) C(O)H,
16) $(C_0$-$C_6)$alkylene-$CO_2H$,
17) $C(O)N(R^b)_2$,
18) $S(O)_mR^a$, and
19) $S(O)_2NR^{10}R^{11}$;

said alkyl, alkenyl, alkynyl, cycloalkyl, aryl, and heterocyclyl is optionally substituted with one, two or three substituents selected from $R^b$, OH, $(C_1$-$C_6)$alkoxy, halogen, $CO_2H$, CN, $O(C=O)C_1$-$C_6$ alkyl, oxo, and $N(R^b)_2$; or two $R^9$s, attached to the same carbon atom are combined to form —$(CH_2)_u$— wherein u is 3 to 6 and one or two of the carbon atoms is optionally replaced by a moiety selected from O, $S(O)_m$, —$N(R^a)C(O)$—, —$N(R^b)$— and —$N(COR^a)$—;

$R^{10}$ and $R^{11}$ are independently selected from:
1) H,
2) (C=O)O$_b$C$_1$-C$_{10}$ alkyl,
3) (C=O)O$_b$C$_3$-C$_8$ cycloalkyl,
4) (C=O)O$_b$aryl,
5) (C=O)O$_b$heterocyclyl,
6) C$_1$-C$_{10}$ alkyl,
7) aryl,
8) C$_2$-C$_{10}$ alkenyl,
9) C$_2$-C$_{10}$ alkynyl,
10) heterocyclyl,
11) C$_3$-C$_8$ cycloalkyl,
12) SO$_2$R$^a$, and
13) (C=O)NR$^b{}_2$, said alkyl, cycloalkyl, aryl, heterocylyl, alkenyl, and alkynyl is optionally substituted with one, two or three substituents selected from R$^8$, or $R^{10}$ and $R^{11}$ can be taken together with the nitrogen to which they are attached to form a monocyclic or bicyclic heterocycle with 5-7 members in each ring and optionally containing, in addition to the nitrogen, one or two additional heteroatoms selected from N, O and S, said monocyclic or bicyclic heterocycle optionally substituted with one, two or three substituents selected from R$^9$;

R$^a$ is independently selected from: (C$_1$-C$_6$)alkyl, (C$_2$-C$_6$)alkenyl, (C$_3$-C$_6$)cycloalkyl, aryl, —(C$_1$-C$_6$)alkylenearyl, heterocyclyl and —(C$_1$-C$_6$)alkyleneheterocyclyl;

R$^b$ is independently selected from: H, (C$_1$-C$_6$)alkyl, aryl, —(C$_1$-C$_6$)alkylenearyl, heterocyclyl, —(C$_1$-C$_6$)alkyleneheterocyclyl, (C$_3$-C$_6$)cycloalkyl, (C=O)OC$_1$-C$_6$ alkyl, (C=O)C$_1$-C$_6$ alkyl or S(O)$_2$R$^a$; and R$^c$ is independently selected from: H, (C$_1$-C$_6$)alkyl, (C$_2$-C$_6$) alkenyl, (C$_3$-C$_6$)cycloalkyl, aryl, —(C$_1$-C$_6$)alkylenearyl, heterocyclyl and —(C$_1$-C$_6$)alkyleneheterocyclyl.

Specific examples of the compounds of the instant invention include:
8-phenyl-10H-furo[2',3':4,5]cyclohepta[1,2-b]pyridin-10-one;
8-chloro-10H-furo[2',3':4,5]cyclohepta[1,2-b]pyridin-10-one;
8-methoxy-10H-furo[2',3':4,5]cyclohepta[1,2-b]pyridin-10-one;
8-phenyl-10H-thieno[2',3':4,5]cyclohepta[1,2-b]pyridin-10-one;
6-phenyl-4H-thieno[3',2':4,5]cyclohepta[1,2-b]pyridin-4-one;

or a pharmaceutical salt thereof.

In another embodiment of the invention, the compounds of the invention include the TFA salts of the following compounds:
8-phenyl-10H-furo[2',3':4,5]cyclohepta[1,2-b]pyridin-10-one;
8-phenyl-10H-thieno[2',3':4,5]cyclohepta[1,2-b]pyridin-10-one; and
6-phenyl-4H-thieno[3',2':4,5]cyclohepta[1,2-b]pyridin-4-one.

The compounds of the present invention may have asymmetric centers, chiral axes, and chiral planes (as described in: E. L. Eliel and S. H. Wilen, *Stereochemistry of Carbon Compounds*, John Wiley & Sons, New York, 1994, pages 1119-1190), and occur as racemates, racemic mixtures, and as individual diastereomers, with all possible isomers and mixtures thereof, including optical isomers, all such stereoisomers being included in the present invention. In addition, the compounds disclosed herein may exist as tautomers and both tautomeric forms are intended to be encompassed by the scope of the invention, even though only one tautomeric structure is depicted.

When any variable (e.g. R$^6$, R$^8$, R$^b$, etc.) occurs more than one time in any constituent, its definition on each occurrence is independent at every other occurrence. Also, combinations of substituents and variables are permissible only if such combinations result in stable compounds. Lines drawn into the ring systems from substituents represent that the indicated bond may be attached to any of the substitutable ring atoms. If the ring system is polycyclic, it is intended that the bond be attached to any of the suitable carbon atoms on the proximal ring only.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. The phrase "optionally substituted with one or more substituents" should be taken to be equivalent to the phrase "optionally substituted with at least one substituent" and in such cases another embodiment will have from zero to three substituents.

As used herein, "alkyl" is intended to include both branched and straight-chain saturated aliphatic hydrocarbon groups having the specified number of carbon atoms. For example, C$_1$-C$_{10}$, as in "C$_1$-C$_{10}$ alkyl" is defined to include groups having 1, 2, 3, 4, 5, 6, 7, 8, 9 or 10 carbons in a linear or branched arrangement. For example, "C$_1$-C$_{10}$ alkyl" specifically includes methyl, ethyl, n-propyl, i-propyl, n-butyl, t-butyl, i-butyl, pentyl, hexyl, heptyl, octyl, nonyl, decyl, and so on. The term "cycloalkyl" means a monocyclic saturated aliphatic hydrocarbon group having the specified number of carbon atoms. For example, "cycloalkyl" includes cyclopropyl, methyl-cyclopropyl, 2,2-dimethyl-cyclobutyl, 2-ethyl-cyclopentyl, cyclohexyl, and so on. In an embodiment of the invention the term "cycloalkyl" includes the groups described immediately above and further includes monocyclic unsaturated aliphatic hydrocarbon groups. For example, "cycloalkyl" as defined in this embodiment includes cyclopropyl, methyl-cyclopropyl, 2,2-dimethyl-cyclobutyl, 2-ethyl-cyclopentyl, cyclohexyl, cyclopentenyl, cyclobutenyl and so on.

The term "alkylene" means a hydrocarbon diradical group having the specified number of carbon atoms. For example, "alkylene" includes —CH$_2$—, —CH$_2$CH$_2$— and the like.

When used in the phrases "C$_1$-C$_6$ aralkyl" and "C$_1$-C$_6$ heteroaralkyl" the term "C$_1$-C$_6$" refers to the alkyl portion of the moiety and does not describe the number of atoms in the aryl and heteroaryl portion of the moiety.

"Alkoxy" represents either a cyclic or non-cyclic alkyl group of indicated number of carbon atoms attached through an oxygen bridge. "Alkoxy" therefore encompasses the definitions of alkyl and cycloalkyl above.

If no number of carbon atoms is specified, the term "alkenyl" refers to a non-aromatic hydrocarbon radical, straight, branched or cyclic, containing from 2 to 10 carbon atoms and at least one carbon to carbon double bond. Preferably one carbon to carbon double bond is present, and up to four non-aromatic carbon-carbon double bonds may be present. Thus, "C$_2$-C$_6$ alkenyl" means an alkenyl radical having from 2 to 6 carbon atoms. Alkenyl groups include ethenyl, propenyl, butenyl, 2-methylbutenyl and cyclohexenyl. The straight, branched or cyclic portion of the alkenyl group may contain double bonds and may be substituted if a substituted alkenyl group is indicated.

The term "alkynyl" refers to a hydrocarbon radical straight, branched or cyclic, containing from 2 to 10 carbon atoms and at least one carbon to carbon triple bond. Up to three carbon-carbon triple bonds may be present. Thus, "$C_2$-$C_6$ alkynyl" means an alkynyl radical having from 2 to 6 carbon atoms. Alkynyl groups include ethynyl, propynyl, butynyl, 3-methylbutynyl and so on. The straight, branched or cyclic portion of the alkynyl group may contain triple bonds and may be substituted if a substituted alkynyl group is indicated.

In certain instances, substituents may be defined with a range of carbons that includes zero, such as ($C_0$-$C_6$)alkylene-aryl. If aryl is taken to be phenyl, this definition would include phenyl itself as well as —$CH_2$Ph, —$CH_2CH_2$Ph, $CH(CH_3)$ $CH_2CH(CH_3)$Ph, and so on.

As used herein, "aryl" is intended to mean any stable monocyclic or bicyclic carbon ring of up to 7 atoms in each ring, wherein at least one ring is aromatic. Examples of such aryl elements include phenyl, naphthyl, tetrahydronaplithyl, indanyl and biphenyl. In cases where the aryl substituent is bicyclic and one ring is non-aromatic, it is understood that attachment is via the aromatic ring.

The term heteroaryl, as used herein, represents a stable monocyclic or bicyclic ring of up to 7 atoms in each ring, wherein at least one ring is aromatic and contains from 1 to 4 heteroatoms selected from the group consisting of O, N and S. Heteroaryl groups within the scope of this definition include but are not limited to: acridinyl, carbazolyl, cinnolinyl, quinoxalinyl, pyrrazolyl, indolyl, benzotriazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetrahydroquinoline. As with the definition of heterocycle below, "heteroaryl" is also understood to include the N-oxide derivative of any nitrogen-containing heteroaryl. In cases where the heteroaryl substituent is bicyclic and one ring is non-aromatic or contains no heteroatoms, it is understood that attachment is via the aromatic ring or via the heteroatom containing ring, respectively.

The term "heterocycle" or "heterocyclyl" as used herein is intended to mean a 3- to 10-membered aromatic or nonaromatic heterocycle containing from 1 to 4 heteroatoms selected from the group consisting of O, N and S, and includes bicyclic groups. "Heterocyclyl" therefore includes the above mentioned heteroaryls, as well as dihydro and tetrathydro analogs thereof. Further examples of "heterocyclyl" include, but are not limited to the following: azetidinyl, benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrahydrothiopyranyl, tetrahydroisoquinolinyl, tetrazolyl, tetrazolopyridyl, thiadiazolyl, thiazolyl, thienyl, triazolyl, 1,4-dioxanyl, hexahydroazepinyl, piperazinyl, piperidinyl, pyridin-2-onyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof. Attachment of a heterocyclyl substituent can occur via a carbon atom or via a heteroatom.

In an embodiment, the term "heterocycle" or "heterocyclyl" as used herein is intended to mean a 5- to 10-membered aromatic or nonaromatic heterocycle containing from 1 to 4 heteroatoms selected from the group consisting of O, N and S, and includes bicyclic groups. "Heterocyclyl" in this embodiment therefore includes the above mentioned heteroaryls, as well as dihydro and tetrathydro analogs thereof. Further examples of "heterocyclyl" include, but are not limited to the following: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrahydrothiopyranyl, tetrahydroisoquinolinyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyridin-2-onyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof. Attachment of a heterocyclyl substituent can occur via a carbon atom or via a heteroatom.

In another embodiment, heterocycle is selected from 2-azepinone, benzimidazolyl, 2-diazapinone, imidazolyl, 2-imidazolidinone, indolyl, isoquinolinyl, morpholinyl, piperidyl, piperazinyl, pyridyl, pyrrolidinyl, 2-piperidinone, 2-pyrimidinone, 2-pyrollidinone, quinolinyl, tetrahydrofuryl, tetrahydroisoquinolinyl, and thienyl.

As appreciated by those of skill in the art, "halo" or "halogen" as used herein is intended to include chloro, fluoro, bromo and iodo.

The alkyl, alkenyl, alkynyl, cycloalkyl, aryl, heteroaryl and heterocyclyl substituents may be substituted or unsubstituted, unless specifically defined otherwise. For example, a ($C_1$-$C_6$) alkyl may be substituted with one, two or three substituents selected from OH, oxo, halogen, alkoxy, dialkylamino, or heterocyclyl, such as morpholinyl, piperidinyl, and so on. In this case, if one substituent is oxo and the other is OH, the following are included in the definition:

—C(=O)$CH_2$CH(OH)$CH_3$, —(C=O)OH, —$CH_2$(OH)$CH_2$CH(O), and so on.

The moiety formed when, in the definition of two $R^8$s or two $R^9$s on the same carbon atom are combined to form —$(CH_2)_u$— is illustrated by the following:

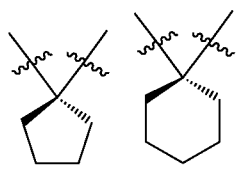

In addition, such cyclic moieties may optionally include one or two heteroatom(s). Examples of such heteroatom-containing cyclic moieties include, but are not limited to:

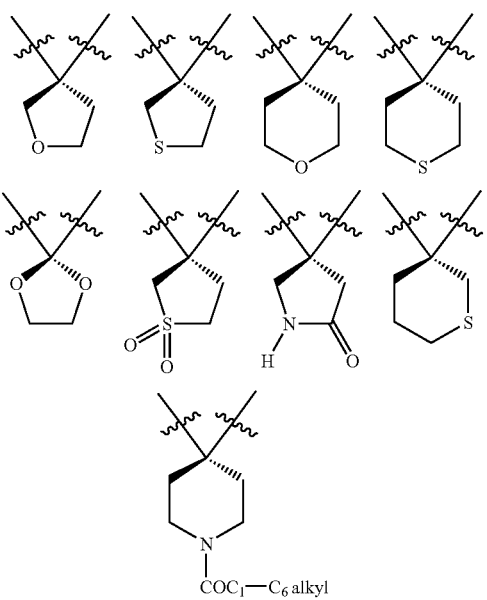

In certain instances, $R^{10}$ and $R^{11}$ are defined such that they can be taken together with the nitrogen to which they are attached to form a monocyclic or bicyclic heterocycle with 5-7 members in each ring and optionally containing, in addition to the nitrogen, one or two additional heteroatoms selected from N, O and S, said heterocycle optionally substituted with one or more substituents selected from $R^9$. Examples of the heterocycles that can thus be formed include, but are not limited to the following, keeping in mind that the heterocycle is optionally substituted with one or more (and in another embodiment, one, two or three) substituents chosen from $R^9$:

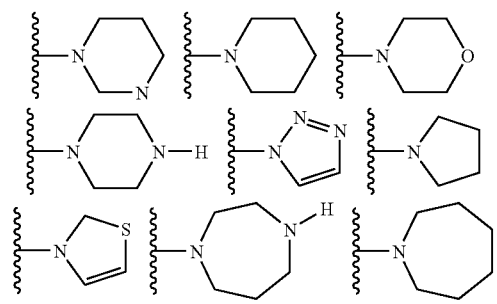

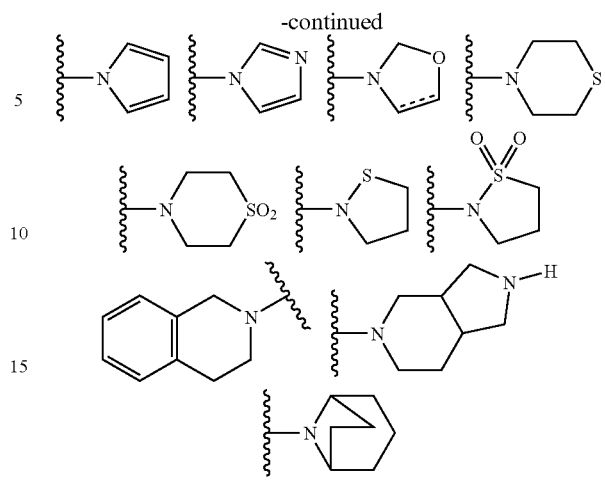

The moiety in Formula I

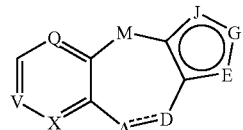

is illustrated by, but not limited to, the following ring systems (note that substituents on C and N atoms in the following structures, although present by the definitions in the compound of Formula I (such as $R^4$, $R^5$, $R^6$, $R^8$ and $R^{10}$), are not illustrated below in order to simplify the illustration):

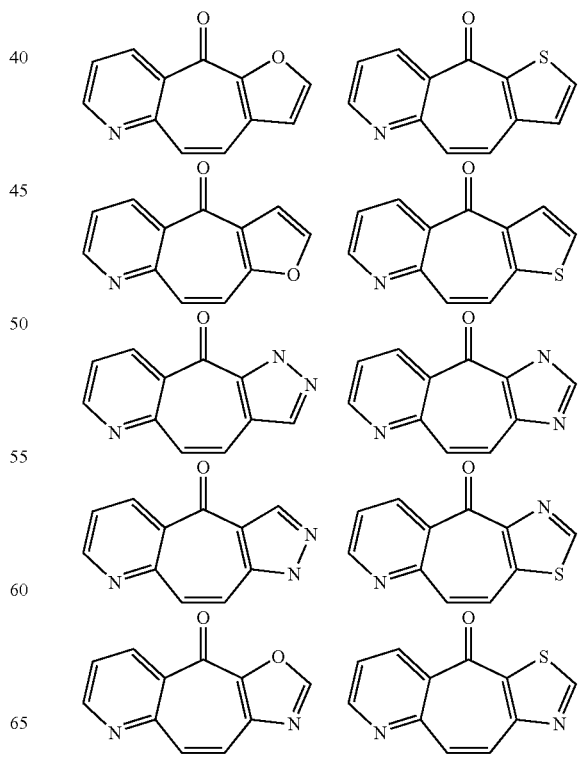

-continued is illustrated by, but not limited to, the following ring systems (note that substituents on C and N atoms in the following structures, although present by the definitions in the compound of Formula I (such as $R^4$, $R^5$, $R^6$, $R^8$ and $R^{10}$), are not illustrated below in order to simplify the illustration):

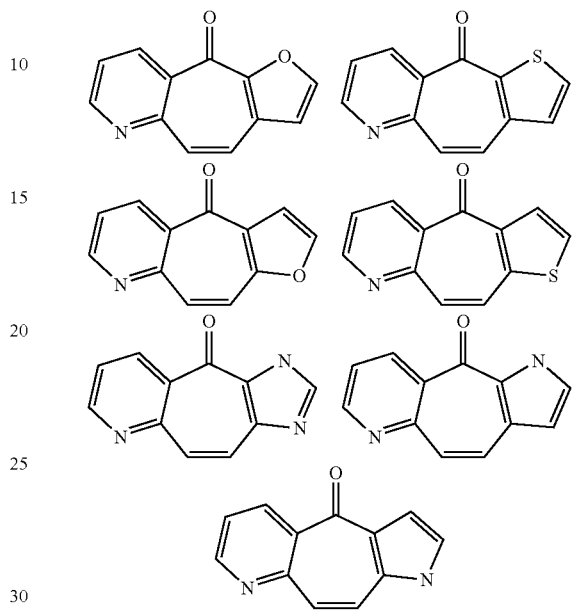

The moiety in Formula II

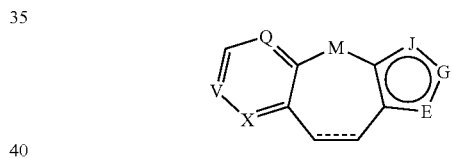

is illustrated by, but not limited to, the following ring systems (note that substituents on C and N atoms in the following structures, although present by the definitions in the compound of Formula II (such as $R^6$, $R^8$ and $R^{10}$), are not illustrated below in order to simplify the illustration):

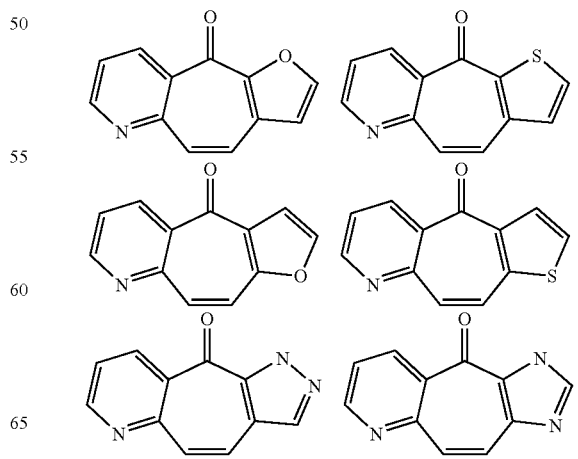

In an embodiment of the compounds of the Formula I, the moiety in Formula I

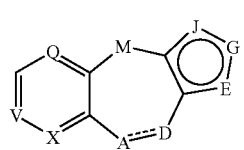

-continued

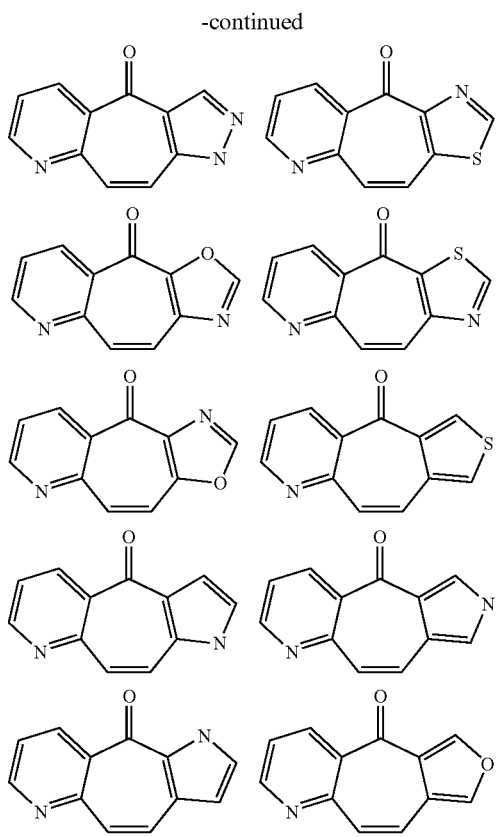

In an embodiment of the compound of the Formula II, the moiety

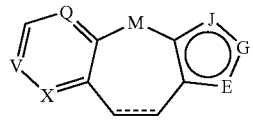

is selected from the following ring systems (note that substituents on C and N atoms in the following structures, although present by the definitions in the compound of Formula II (such as $R^6$, $R^8$ and $R^{10}$), are not illustrated below in order to simplify the illustration):

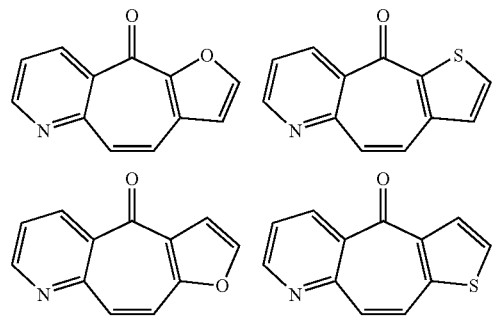

-continued

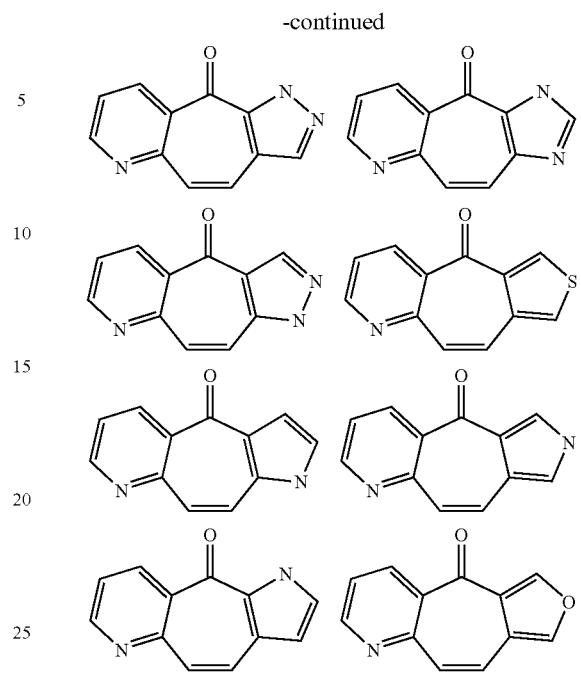

In a further embodiment of the compounds of the Formula II, the moiety in Formula II

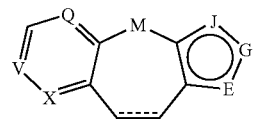

is illustrated by, but not limited to, the following ring systems (note that substituents on C and N atoms in the following structures, although present by the definitions in the compound of Formula II (such as $R^6$, $R^8$ and $R^{10}$), are not illustrated below in order to simplify the illustration):

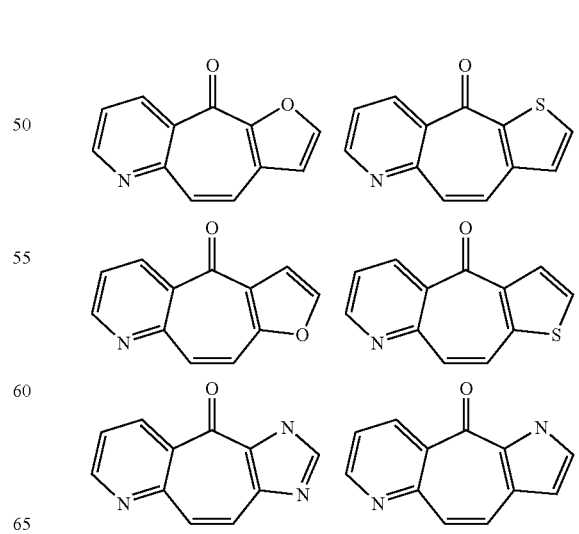

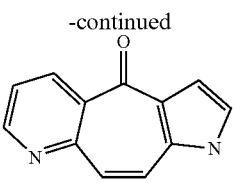

The moiety in Formula III

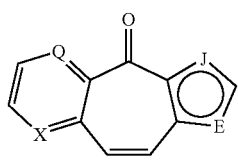

is illustrated by, but not limited to, the following ring systems (note that substituents on C and N atoms in the following structures, although present by the definitions in the compound of Formula III (such as $R^6$, $R^8$ and $R^{10}$), are not illustrated below in order to simplify the illustration):

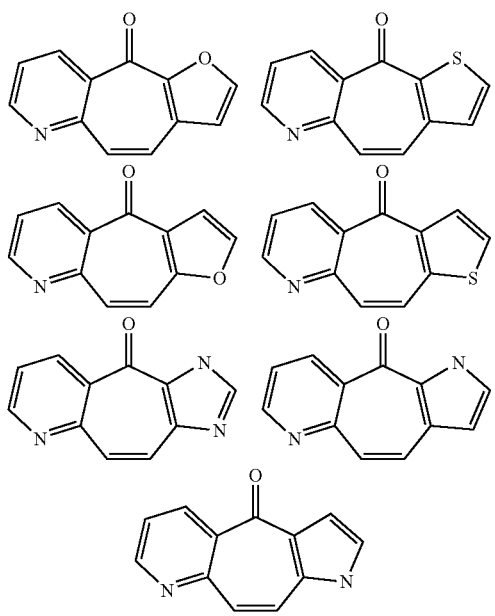

In an embodiment of the compound of the Formula I, the dashed line represents a double bond.

In an embodiment of the compounds of Formula I, $R^1$ is selected from Cl, aryl, heterocyclic, methoxy and $NR^{10}R^{11}$; said aryl and heterocyclic group optionally substituted with one to five substituents, each substituent independently selected from $R^8$. In a further embodiment of the compounds of Formula I, $R^1$ is selected from aryl, heterocyclic, and $NR^{10}R^{11}$; said aryl and heterocyclic group optionally substituted with one to five substituents, each substituent independently selected from $R^8$. In another embodiment of the Formulae I and II, $R^1$ is selected from aryl and heterocyclic; said aryl and heterocyclic group optionally substituted with one to five substituents, each substituent independently selected from $R^8$.

In an embodiment of the compound of the Formula I, $R^2$ and $R^3$ are hydrogen.

In an embodiment of the compound of the Formula I, $R^4$ and $R^5$ are hydrogen.

In an embodiment of the compound of the Formula I, $R^6$ is selected from hydrogen, halogen, $C_{1-6}$alkyl, OH, —O—$C_{1-6}$alkyl, —O—C(=O)$C_{1-6}$ alkyl, —O-aryl, $S(O)_m R^a$ and $NR^{10}R^{11}$, each alkyl and aryl optionally substituted with one to five substituents, each substituent independently selected from $R^8$.

In an embodiment of the Formula I, $R^6$ is hydrogen.

In an embodiment of the Formula II, the dashed line represents a double bond, V is CH, Q is CH, M is C=O and $R^4$ is hydrogen.

In an embodiment of the Formula III, Q is CH.

Included in the instant invention is the free form of compounds of Formula I, as well as the pharmaceutically acceptable salts and stereoisomers thereof. Some of the specific compounds exemplified herein are the protonated salts of amine compounds. The term "free form" refers to the amine compounds in non-salt form. The encompassed pharmaceutically acceptable salts not only include the salts exemplified for the specific compounds described herein, but also all the typical pharmaceutically acceptable salts of the free form of compounds of Formula I. The free form of the specific salt compounds described may be isolated using techniques known in the art. For example, the free form may be regenerated by treating the salt with a suitable dilute aqueous base solution such as dilute aqueous NaOH, potassium carbonate, ammonia and sodium bicarbonate. The free forms may differ from their respective salt forms somewhat in certain physical properties, such as solubility in polar solvents, but the acid and base salts are otherwise pharmaceutically equivalent to their respective free forms for purposes of the invention.

The pharmaceutically acceptable salts of the instant compounds can be synthesized from the compounds of this invention which contain a basic or acidic moiety by conventional chemical methods. Generally, the salts of the basic compounds are prepared either by ion exchange chromatography or by reacting the free base with stoichiometric amounts or with an excess of the desired salt-forming inorganic or organic acid in a suitable solvent or various combinations of solvents. Similarly, the salts of the acidic compounds are formed by reactions with the appropriate inorganic or organic base.

Thus, pharmaceutically acceptable salts of the compounds of this invention include the conventional non-toxic salts of the compounds of this invention as formed by reacting a basic instant compound with an inorganic or organic acid. For example, conventional non-toxic salts include those derived from inorganic acids such as hydrochloric, hydrobromic, sulfuric, sulfamic, phosphoric, nitric and the like, as well as salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like.

When the compound of the present invention is acidic, suitable "pharmaceutically acceptable salts" refers to salts prepared form pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particularly preferred are the ammonium, calcium, magnesium, potassium and sodium salts. Salts derived from pharmaceutically acceptable organic non-toxic bases include salts of primary, secondary and tertiary amines, substituted amines including naturally occurring substituted amines, cyclic amines and basic ion exchange resins, such as arginine, betaine caffeine, choline, N,N¹-dibenzylethylenediamine, diethylamin, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine tripropylamine, tromethamine and the like. When the compound of the present invention is acidic, the term "free form" refers to the compound in its non-salt form, such that the acidic functionality is still protonated.

The preparation of the pharmaceutically acceptable salts described above and other typical pharmaceutically acceptable salts is more fully described by Berg et al., "Pharmaceutical Salts," *J. Pharm. Sci.,* 1977:66:1-19.

It will also be noted that the compounds of the present invention may potentially be internal salts or zwitterions, since under physiological conditions a deprotonated acidic moiety in the compound, such as a carboxyl group, may be anionic, and this electronic charge might then be balanced off internally against the cationic charge of a protonated or alkylated basic moiety, such as a quaternary nitrogen atom. An isolated compound having internally balance charges, and thus not associated with a intermolecular counterion, may also be considered the "free form" of a compound.

Certain abbreviations, used in the Schemes and Examples, are defined below:

| | |
|---|---|
| APCI | Atmospheric pressure chemical ionization |
| DMF | Dimethylformamide |
| DMSO | Dimethyl sulfoxide |
| EtOAc | Ethyl acetate |
| LCMS | Liquid chromatographic mass spectrometry |
| MPLC | Medium pressure liquid chromatography |
| NBS | N-bromosuccinamide |
| TFA | Trifluoroacetic acid |
| TFA | Trifluoroacetic anhydride |

The compounds of this invention may be prepared by employing reactions as shown in the following schemes, in addition to other standard manipulations that are known in the literature or exemplified in the experimental procedures. The illustrative schemes below, therefore, are not limited by the compounds listed or by any particular substituents employed for illustrative purposes. Substituent numbering as shown in the schemes does not necessarily correlate to that used in the claims and often, for clarity, a single substituent is shown attached to the compound where multiple substituents are allowed under the definitions of Formula I hereinabove.

Schemes

Preparation of the instant compounds is illustrated in Schemes F to I. Thus, in Scheme A, displacement of the thioester of intermediate A-1 with a suitable heteroaryl aldehyde boronic acid provides intermediate A-2, which undergoes cyclization in the presence of a strong base to yield the instant compound A-3. Schemes B and C illustrate analogous preparations of regioisomeric instant compounds, while Scheme D illustrates incorporation of two heteroatoms (via a pyrazolyl boraonic acid).

Scheme E illustrates the preparation of the instant compounds having ring element M as an amido moiety. This homologation is accomplished by converting the carbonyl of a compound of the instant invention to the hydroxylamine of intermediate E-1, which then rearranges upon treatment with PPA to provide the instant compounds E-2 and E-3.

Preparation of the instant compounds wherein ring element A is N is illustrated in Scheme F. Thus, 2-aminonicotinic acid is converted to the diazaisocoumarin F-1. Subsequent annulation with a in situ generated lithio-arene provides the intermediate/instant compound F-2, which can then be functionalized as illustrated in the above schemes.

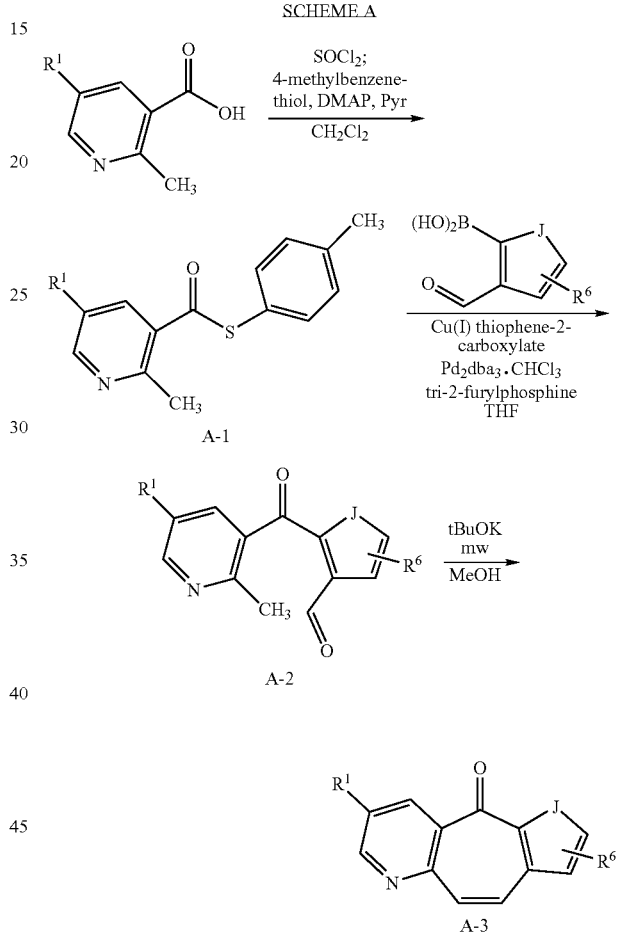

J is O, NR¹⁰ or S

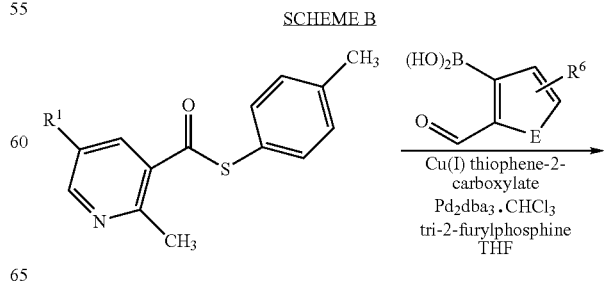

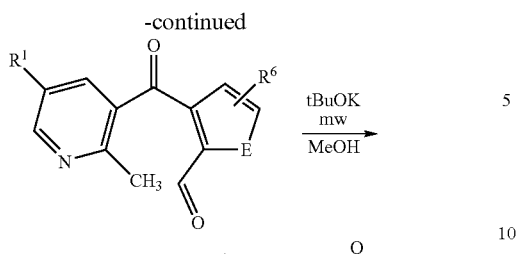
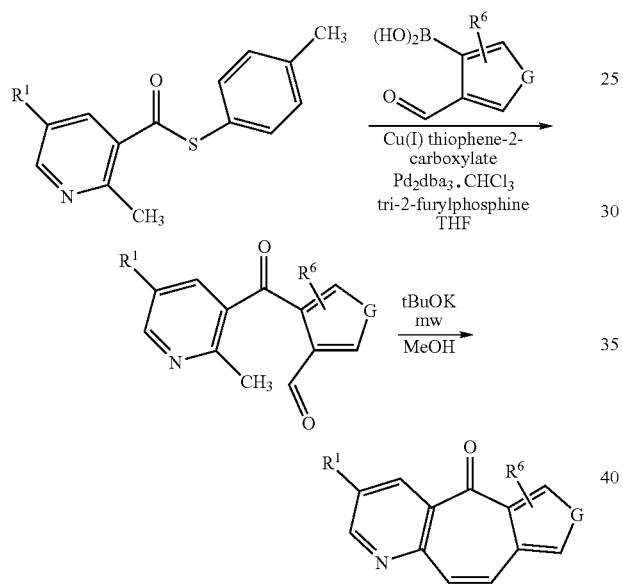
E is O, NR[10] or S
SCHEME C
G is O, NR[10] or S
SCHEME D
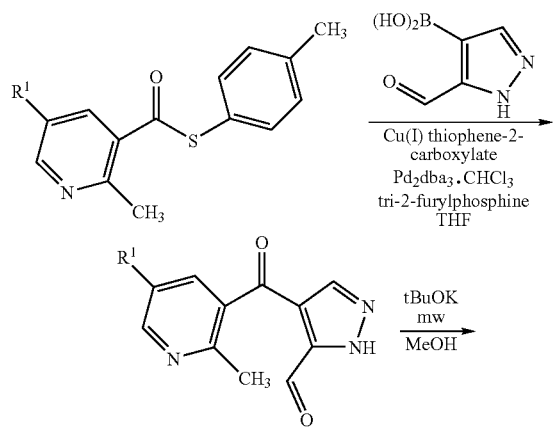
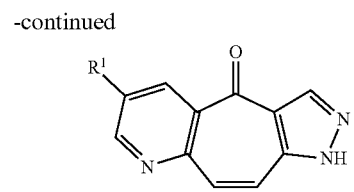
SCHEME E
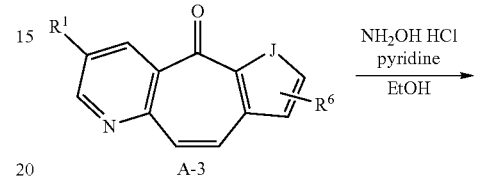
A-3
SCHEME F
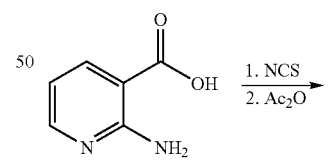
F-1
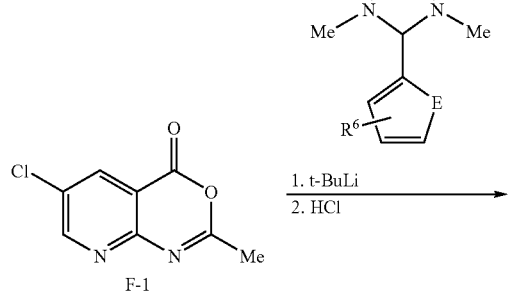

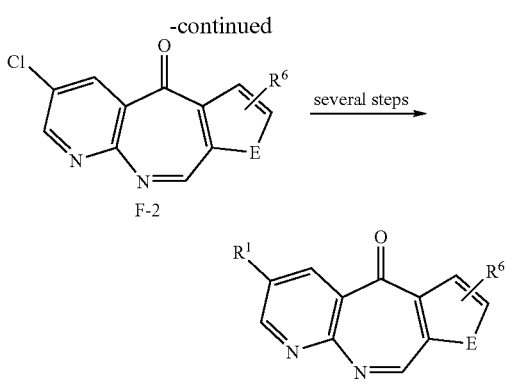

Utilities

The compounds of the invention are useful to bind to and/or modulate the activity of a tyrosine kinase, in particular, a receptor tyrosine kinase. In an embodiment, the receptor tyrosine kinase is a member of the MET subfamily. In a further embodiment, the MET is human MET, although the activity of receptor tyrosine kinases from other organisms may also be modulated by the compounds of the present invention. In this context, modulate means either increasing or decreasing kinase activity of MET. In an embodiment, the compounds of the instant invention inhibit the kinase activity of MET.

The compounds of the invention find use in a variety of applications. As will be appreciated by those skilled in the art, the kinase activity of MET may be modulated in a variety of ways; that is, one can affect the phosphorylation/activation of MET either by modulating the initial phosphorylation of the protein or by modulating the autophosphorylation of the other active sites of the protein. Alternatively, the kinase activity of MET may be modulated by affecting the binding of a substrate of MET phosphorylation.

The compounds of the invention are used to treat or prevent cellular proliferation diseases. Disease states which can be treated by the methods and compositions provided herein include, but are not limited to, cancer (further discussed below), autoimmune disease, arthritis, graft rejection, inflammatory bowel disease, proliferation induced after medical procedures, including, but not limited to, surgery, angioplasty, and the like. It is appreciated that in some cases the cells may not be in a hyper- or hypoproliferation state (abnormal state) and still require treatment. Thus, in one embodiment, the invention herein includes application to cells or individuals which are afflicted or may eventually become afflicted with any one of these disorders or states.

The compounds, compositions and methods provided herein are particularly deemed useful for the treatment and prevention of cancer including solid tumors such as skin, breast, brain, cervical carcinomas, testicular carcinomas, etc. In an embodiment, the instant compounds are useful for treating cancer. In particular, cancers that may be treated by the compounds, compositions and methods of the invention include, but are not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma, familial adenomatous polyposis [FAP]); Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma. Thus, the term "cancerous cell" as provided herein, includes a cell afflicted by any one of the above-identified conditions. In another embodiment, the compounds of the instant invention are useful for treating or preventing cancer selected from: histiocytic lymphoma, lung adenocarcinoma, small cell lung cancers, pancreatic cancer, liver cancer, gastric cancer, colon cancer, multiple myeloma, glioblastomas and breast carcinoma. In still another embodiment, the compounds of the instant invention are useful for treating cancer selected from: histiocytic lymphoma, lung adenocarcinoma, small cell lung cancers, pancreatic cancer, liver cancer, gastric cancer, colon cancer, multiple myeloma, glioblastomas and breast carcinoma.

In another embodiment, the compounds of the instant invention are useful for the prevention or modulation of the metastases of cancer cells and cancer. In particular, the compounds of the instant invention are useful to prevent or modulate the metastases of ovarian cancer, childhood hepatocellular carcinoma, metastatic head and neck squamous cell carcinomas, gastric cancers, breast cancer, colorectal cancer, cervical cancer, lung cancer, nasopharyngeal cancer, pancreatic cancer, glioblastoma and sarcomas.

The compounds of this invention may be administered to mammals, preferably humans, either alone or in combination with pharmaceutically acceptable carriers, excipients or diluents, in a pharmaceutical composition, according to standard pharmaceutical practice. The compounds can be administered orally or parenterally, including the intravenous, intramuscular, intraperitoneal, subcutaneous, rectal and topical routes of administration.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, microcrystalline cellulose, sodium crosscarmellose, corn starch, or alginic acid; binding agents, for example starch, gelatin, polyvinyl-pyrrolidone or acacia, and lubricating agents, for example, magnesium stearate, stearic acid or talc. The tablets may be uncoated or they may be coated by known techniques to mask the unpleasant taste of the drug or delay disintegration and absorption in the gastrointestinal tract and thereby provide a sustained action over a longer period. For example, a water soluble taste masking material such as hydroxypropyl-methylcellulose or hydroxypropylcellulose, or a time delay material such as ethyl cellulose, cellulose acetate butyrate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening, flavoring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

The pharmaceutical compositions may be in the form of a sterile injectable aqueous solutions. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulation.

The injectable solutions or microemulsions may be introduced into a patient's blood stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, for example as a solution in 1,3-butane diol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of Formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, etc., containing the compound of Formula I are employed. (For purposes of this application, topical application shall include mouth washes and gargles.)

The compounds for the present invention can be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

When a compound according to this invention is administered into a human subject, the daily dosage will normally be determined by the prescribing physician with the dosage generally varying according to the age, weight, sex and response of the individual patient, as well as the severity of the patient's symptoms.

In one exemplary application, a suitable amount of compound is administered to a mammal undergoing treatment for cancer. Administration occurs in an amount between about 0.1 mg/kg of body weight to about 60 mg/kg of body weight per day, preferably of between 0.5 mg/kg of body weight to about 40 mg/kg of body weight per day.

The instant compounds are also useful in combination with known therapeutic agents and anti-cancer agents. For example, instant compounds are useful in combination with known anti-cancer agents. Combinations of the presently disclosed compounds with other anti-cancer or chemotherapeutic agents are within the scope of the invention. Examples of such agents can be found in *Cancer Principles and Practice of Oncology* by V. T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Such anti-cancer agents include, but are not limited to, the following: estrogen receptor modulators, androgen receptor modulators, retinoid receptor modulators, cytotoxic/cytostatic agents, antiproliferative agents, prenyl-protein transferase inhibitors, HMG-CoA reductase inhibitors and other angiogenesis inhibitors, inhibitors of cell proliferation and survival signaling, apoptosis inducing agents and agents that interfere with cell cycle checkpoints. The instant compounds are particularly useful when co-administered with radiation therapy.

In an embodiment, the instant compounds are also useful in combination with known anti-cancer agents including the following: estrogen receptor modulators, androgen receptor modulators, retinoid receptor modulators, cytotoxic agents, antiproliferative agents, prenyl-protein transferase inhibitors, HMG-CoA reductase inhibitors, HIV protease inhibitors, reverse transcriptase inhibitors, and other angiogenesis inhibitors.

"Estrogen receptor modulators" refers to compounds that interfere with or inhibit the binding of estrogen to the receptor, regardless of mechanism. Examples of estrogen receptor modulators include, but are not limited to, tamoxifen, raloxifene, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenyl-hydrazone, and SH646.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"Retinoid receptor modulators" refers to compounds which interfere or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylornithine, ILX23-7553, trans-N-(4'-hydroxyphenyl) retinamide, and N-4-carboxyphenyl retinamide.

"Cytotoxic/cytostatic agents" refer to compounds which cause cell death or inhibit cell proliferation primarily by interfering directly with the cell's functioning or inhibit or interfere with cell mytosis, including alkylating agents, tumor necrosis factors, intercalators, hypoxia activatable compounds, microtubule inhibitors/microtubule-stabilizing agents, inhibitors of mitotic kinesins, inhibitors of histone deacetylase, inhibitors of kinases involved in mitotic progression, antimetabolites; biological response modifiers; hormonal/anti-hormonal therapeutic agents, haematopoietic growth factors, monoclonal antibody targeted therapeutic agents, topoisomerase inhibitors, proteasome inhibitors and ubiquitin ligase inhibitors.

Examples of cytotoxic agents include, but are not limited to, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX100, (trans, trans, trans)-bis-mu-(hexane-1,6-diamine)-mu-[diamine-platinum (II)]bis[diamine(chloro)platinum (II)]tetrachloride, diarizidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycaminomycin, annamycin, galarubicin, elinafide, MEN10755, and 4-demethoxy-3-deamino-3-aziridinyl-4-methylsulphonyl-daunorubicin (see WO 00/50032).

An example of a hypoxia activatable compound is tirapazamine.

Examples of proteasome inhibitors include but are not limited to lactacystin and bortezomib.

Examples of microtubule inhibitors/microtubule-stabilising agents include paclitaxel, vindesine sulfate, 3',4'-didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl)benzene sulfonamide, anhydrovinblastine, N,N-dimethyl-L-valyl-L-valyl-N-methyl-L-valyl-L-prolyl-L-proline-t-butylamide, TDX258, the epothilones (see for example U.S. Pat. Nos. 6,284,781 and 6,288,237) and BMS188797.

Some examples of topoisomerase inhibitors are topotecan, hycaptamine, irinotecan, rubitecan, 6-ethoxypropionyl-3',4'-O-exo-benzylidene-chartreusin, 9-methoxy-N,N-dimethyl-5-nitropyrazolo[3,4,5-kl]acridine-2-(6H) propanamine, 1-amino-9-ethyl-5-fluoro-2,3-dihydro-9-hydroxy-4-methyl-1H, 12H-benzo[de]pyrano[3',4':b,7]-indolizino[1,2b]quinoline-10,13(9H, 15H)dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, (5a,5aB,8aa,9b)-9-[2-[N-[2-(dimethylamino)ethyl]-N-methylamino]ethyl]-5-[4-hydr0xy-3,5-dimethoxyphenyl]-5,5a,6,8,8a,9-hexohydrofuro(3',4':6,7)naphtho(2,3-d)-1,3-dioxol-6-one, 2,3-(methylenedioxy)-5-methyl-7-hydroxy-8-methoxybenzo[c]-phenanthridinium, 6,9-bis[[(2-aminoethyl)amino]benzo[g]isoquinoline-5,10-dione, 5-(3-aminopropylamino)-7,10-dihydroxy-2-(2-hydroxyethylaminomethyl)-6H-pyrazolo[4,5,1-de]acridin-6-one, N-[1-[2(diethylamino)ethylamino]-7-methoxy-9-oxo-9H-thioxanthen-4-ylmethyl] formamide, N-(2-(dimethylamino)ethyl)acridine-4-carboxamide, 6-[[2-(dimethylamino)ethyl]amino]-3-hydroxy-7H-indeno[2,1-c]quinolin-7-one, and dimesna.

Examples of inhibitors of mitotic kinesins, and in particular the human mitotic kinesin KSP, are described in PCT Publications WO 01/30768, WO 01/98278, WO 03/050,064, WO 03/050,122, WO 03/049,527, WO 03/049,679, WO 03/049,678 and WO 03/39460 and pending PCT Appl. Nos. US03/06403 (filed Mar. 4, 2003), US03/15861 (filed May 19, 2003), US03/15810 (filed May 19, 2003), US03/18482 (filed Jun. 12, 2003) and US03/18694 (filed Jun. 12, 2003). In an embodiment inhibitors of mitotic kinesins include, but are not limited to inhibitors of KSP, inhibitors of MKLP1, inhibitors of CENP-E, inhibitors of MCAK, inhibitors of Kif14, inhibitors of Mphosph1 and inhibitors of Rab6-KIFL.

Examples of "histone deacetylase inhibitors" include, but are not limited to, SAHA, TSA, oxamflatin, PXD101, MG98, valproic acid and scriptaid. Further reference to other histone deacetylase inhibitors may be found in the following manuscript; Miller, T. A. et al. J. Med. Chem. 46 (24):5097-5116 (2003).

"Inhibitors of kinases involved in mitotic progression" include, but are not limited to, inhibitors of aurora kinase, inhibitors of Polo-like kinases (PLK) (in particular inhibitors of PLK-1), inhibitors of bub-1 and inhibitors of bub-R1.

"Antiproliferative agents" includes antisense RNA and DNA oligonucleotides such as G3139, ODN698, RVASK-RAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydrobenzofuryl)sulfonyl]-N'-(3,4-dichlorophenyl)urea, N6-[4-deoxy-4-[N2-[2(E),4(E)-tetradecadienoyl]glycylamino]-L-glycero-B-L-manno-heptopyranosyl]adenine, aplidine, ecteinascidin, troxacitabine, 4-[2-amino-4-oxo-4,6,7,8-tetrahydro-3H-pyrimidino[5,4-b][1,4]thiazin-6-yl-(S)-ethyl]-2,5-thienoyl-L-glutamic acid, aminopterin, 5-fluorouracil, alanosine, 11-acetyl-8-(carbamoyloxymethyl)-4-formyl-6-methoxy-14-oxa-1,11-diazatetracyclo(7.4.1.0.0)-tetradeca-2,4,6-trien-9-yl acetic acid ester, swainsonine, lometrexol, dexrazoxane, methioninase, 2'-cyano-2'-deoxy-N4-palmitoyl-1-B-D-arabino furanosyl cytosine and 3-aminopyridine-2-carboxaldehyde thiosemicarbazone.

Examples of monoclonal antibody targeted therapeutic agents include those therapeutic agents which have cytotoxic agents or radioisotopes attached to a cancer cell specific or target cell specific monoclonal antibody. Examples include Bexxar.

"HMG-CoA reductase inhibitors" refers to inhibitors of 3-hydroxy-3-methylglutaryl-CoA reductase. Examples of HMG-CoA reductase inhibitors that may be used include but are not limited to lovastatin (MEVACOR®; see U.S. Pat. Nos. 4,231,938, 4,294,926 and 4,319,039), simvastatin (ZOCOR®; see U.S. Pat. Nos. 4,444,784, 4,820,850 and 4,916,239), pravastatin (PRAVACHOL®; see U.S. Pat. Nos. 4,346,227, 4,537,859, 4,410,629, 5,030,447 and 5,180,589), fluvastatin (LESCOL®; see U.S. Pat. Nos. 5,354,772, 4,911,165, 4,929,437, 5,189,164, 5,118,853, 5,290,946 and 5,356,896) and atorvastatin (LIPITOR®; see U.S. Pat. Nos. 5,273,995, 4,681,893, 5,489,691 and 5,342,952). The structural formulas of these and additional HMG-CoA reductase inhibitors that may be used in the instant methods are described at page 87 of M. Yalpani, "Cholesterol Lowering Drugs", Chemistry & Industry, pp. 85-89 (5 Feb. 1996) and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefor the use of such salts, esters, open-acid and lactone forms is included within the scope of this invention.

"Prenyl-protein transferase inhibitor" refers to a compound which inhibits any one or any combination of the prenyl-protein transferase enzymes, including farnesyl-protein transferase (FPTase), geranylgeranyl-protein transferase type I (GGPTase-I), and geranylgeranyl-protein transferase type-II (GGPTase-II, also called Rab GGPTase).

Examples of prenyl-protein transferase inhibitors can be found in the following publications and patents: WO 96/30343, WO 97/18813, WO 97/21701, WO 97/23478, WO 97/38665, WO 98/28980, WO 98/29119, WO 95/32987, U.S. Pat. No. 5,420,245, U.S. Pat. No. 5,523,430, U.S. Pat. No. 5,532,359, U.S. Pat. No. 5,510,510, U.S. Pat. No. 5,589,485, U.S. Pat. No. 5,602,098, European Patent Publ. 0 618 221, European Patent Publ. 0 675 112, European Patent Publ. 0 604 181, European Patent Publ. 0 696 593, WO 94/19357, WO 95/08542, WO 95/11917, WO 95/12612, WO 95/12572, WO 95/10514, U.S. Pat. No. 5,661,152, WO 95/10515, WO 95/10516, WO 95/24612, WO 95/34535, WO 95/25086, WO 96/05529, WO 96/06138, WO 96/06193, WO 96/16443, WO 96/21701, WO 96/21456, WO 96/22278, WO 96/24611, WO 96/24612, WO 96/05168, WO 96/05169, WO 96/00736, U.S. Pat. No. 5,571,792, WO 96/17861, WO 96/33159, WO 96/34850, WO 96/34851, WO 96/30017, WO 96/30018, WO 96/30362, WO 96/30363, WO 96/31111, WO 96/31477, WO 96/31478, WO 96/31501, WO 97/00252, WO 97/03047, WO 97/03050, WO 97/04785, WO 97/02920, WO 97/17070, WO 97/23478, WO 97/26246, WO 97/30053, WO 97/44350, WO 98/02436, and U.S. Pat. No. 5,532,359. For an example of the role of a prenyl-protein transferase inhibitor on angiogenesis see *European J. of Cancer*, Vol. 35, No. 9, pp. 1394-1401 (1999).

"Angiogenesis inhibitors" refers to compounds that inhibit the formation of new blood vessels, regardless of mechanism. Examples of angiogenesis inhibitors include, but are not limited to, tyrosine kinase inhibitors, such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, interferon-α, interleukin-12, pentosan polysulfate, cyclooxygenase inhibitors, including nonsteroidal anti-inflammatories (NSAIDs) like aspirin and ibuprofen as well as selective cyclooxy-genase-2 inhibitors like, celecoxib and rofecoxib (*PNAS*, Vol. 89, p. 7384 (1992); *JNCI*, Vol. 69, p. 475 (1982); *Arch. Opthalmol.*, Vol. 108, p. 573 (1990); *Anat. Rec.*, Vol. 238, p. 68 (1994); *FEBS Letters*, Vol. 372, p. 83 (1995); *Clin, Orthop.* Vol. 313, p. 76 (1995); *J. Mol. Endocrinol.*, Vol. 16, p. 107 (1996); *Jpn. J. Pharmacol.*, Vol. 75, p. 105 (1997); *Cancer Res.*, Vol. 57, p. 1625 (1997); *Cell*, Vol. 93, p. 705 (1998); *Intl. J. Mol. Med.*, Vol. 2, p. 715 (1998); *J. Biol. Chem.*, Vol. 274, p. 9116 (1999)), steroidal anti-inflammatories (such as corticosteroids, mineralocorticoids, dexamethasone, prednisone, prednisolone, methylpred, betamethasone), carboxyamidotriazole, combretastatin A-4, squalamine, 6-O-chloroacetyl-carbonyl)-fumagillol, thalidomide, angiostatin, troponin-1, angiotensin II antagonists (see Fernandez et al., *J. Lab. Clin. Med.* 105:141-145 (1985)), and antibodies to VEGF (see, *Nature Biotechnology*, Vol. 17, pp. 963-968 (October 1999); Kim et al., *Nature*, 362, 841-844 (1993); WO 00/44777; and WO 00/61186).

Other therapeutic agents that modulate or inhibit angiogenesis and may also be used in combination with the compounds of the instant invention include agents that modulate or inhibit the coagulation and fibrinolysis systems (see review in *Clin. Chem. La. Med.* 38:679-692 (2000)). Examples of such agents that modulate or inhibit the coagulation and fibrinolysis pathways include, but are not limited to, heparin (see *Thromb. Haemost.* 80:10-23 (1998)), low molecular weight heparins and carboxypeptidase U inhibitors (also known as inhibitors of active thrombin activatable fibrinolysis inhibitor [TAFIa]) (see *Thrombosis Res.* 101:329-354 (2001)). TAFIa inhibitors have been described in PCT Publication WO 03/013,526 and U.S. Ser. No. 60/349,925 (filed Jan. 18, 2002).

"Agents that interfere with cell cycle checkpoints" refer to compounds that inhibit protein kinases that transduce cell cycle checkpoint signals, thereby sensitizing the cancer cell to DNA damaging agents. Such agents include inhibitors of ATR, ATM, the Chk1 and Chk2 kinases and cdk and cdc kinase inhibitors and are specifically exemplified by 7-hydroxystaurosporin, flavopiridol, CYC202 (Cyclacel) and BMS-387032.

"Inhibitors of cell proliferation and survival signaling pathway" refer to pharmaceutical agents that inhibit cell surface receptors and signal transduction cascades downstream of those surface receptors. Such agents include inhibitors of inhibitors of EGFR (for example gefitinib and erlotinib), inhibitors of ERB-2 (for example trastuzumab), inhibitors of IGFR, inhibitors of cytokine receptors, inhibitors of MET, inhibitors of PI3K (for example LY294002), serine/threonine kinases (including but not limited to inhibitors of Akt such as described in WO 02/083064, WO 02/083139, WO 02/083140 and WO 02/083138), inhibitors of Raf kinase (for example BAY-43-9006), inhibitors of MEK (for example CI-1040 and PD-098059) and inhibitors of mTOR (for example Wyeth CCI-779). Such agents include small molecule inhibitor compounds and antibody antagonists.

"Apoptosis inducing agents" include activators of TNF receptor family members (including the TRAIL receptors).

The invention also encompasses combinations with NSAID's which are selective COX-2 inhibitors. For purposes of this specification NSAID's which are selective inhibitors of COX-2 are defined as those which possess a specificity for inhibiting COX-2 over COX-1 of at least 100 fold as measured by the ratio of $IC_{50}$ for COX-2 over $IC_{50}$ for COX-1 evaluated by cell or microsomal assays. Such compounds include, but are not limited to those disclosed in U.S. Pat. No. 5,474,995, U.S. Pat. No. 5,861,419, U.S. Pat. No. 6,001,843, U.S. Pat. No. 6,020,343, U.S. Pat. No. 5,409,944, U.S. Pat. No. 5,436,265, U.S. Pat. No. 5,536,752, U.S. Pat. No. 5,550, 142, U.S. Pat. No. 5,604,260, U.S. Pat. No. 5,698,584, U.S. Pat. No. 5,710,140, WO 94/15932, U.S. Pat. No. 5,344,991, U.S. Pat. No. 5,134,142, U.S. Pat. No. 5,380,738, U.S. Pat. No. 5,393,790, U.S. Pat. No. 5,466,823, U.S. Pat. No. 5,633, 272, and U.S. Pat. No. 5,932,598, all of which are hereby incorporated by reference.

Inhibitors of COX-2 that are particularly useful in the instant method of treatment are: 3-phenyl-4-(4-(methylsulfonyl)phenyl)-2-(5H)-furanone; and 5-chloro-3-(4-methylsulfonyl)-phenyl-2-(2-methyl-5-pyridinyl)pyridine; or a pharmaceutically acceptable salt thereof.

Compounds that have been described as specific inhibitors of COX-2 and are therefore useful in the present invention include, but are not limited to: parecoxib, CELEBREX® and BEXTRA® or a pharmaceutically acceptable salt thereof.

Other examples of angiogenesis inhibitors include, but are not limited to, endostatin, ukrain, ranpirnase, IM862, 5-methoxy-4-[2-methyl-3-(3-methyl-2-butenyl)oxiranyl]-1-oxas-piro[2,5]oct-6-yl(chloroacetyl)carbamate, acetyldinanaline, 5-amino-1-[[3,5-dichloro-4-(4-chlorobenzoyl)-phenyl]methyl]-1H-1,2,3-triazole-4-carboxamide, CM101, squalamine, combretastatin, RPI4610, NX31838, sulfated mannopentaose phosphate, 7,7-(carbonyl-bis[imino-N-methyl-4,2-pyrrolocarbonylimino[N-methyl-4,2-pyrrole]-carbonylimino]-bis-(1,3-naphthalene disulfonate), and 3-[(2,4-dimethylpyrrol-5-yl)methylene]-2-indolinone (SU5416).

As used above, "integrin blockers" refers to compounds which selectively antagonize, inhibit or counteract binding of a physiological ligand to the $\alpha_v\beta_3$ integrin, to compounds which selectively antagonize, inhibit or counteract binding of a physiological ligand to the $\alpha_v\beta_5$ integrin, to compounds which antagonize, inhibit or counteract binding of a physiological ligand to both the $\alpha_v\beta_3$ integrin and the $\alpha_v\beta_5$ integrin, and to compounds which antagonize, inhibit or counteract the activity of the particular integrin(s) expressed on capillary endothelial cells. The term also refers to antagonists of the $\alpha_v\beta_6$, $\alpha_v\beta_8$, $\alpha_1\beta_1$, $\alpha_2\beta_1$, $\alpha_5\beta_1$, $\alpha_6\beta_1$, and $\alpha_6\beta_4$ integrins. The term also refers to antagonists of any combination of $\alpha_v\beta_3$, $\alpha_v\beta_5$, $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins.

Some specific examples of tyrosine kinase inhibitors include N-(trifluoromethylphenyl)-5-methylisoxazol-4-carboxamide, 3-[(2,4-dimethylpyrrol-5-yl)methylidenyl)indolin-2-one, 17-(allylamino)-17-demethoxygeldanamycin, 4-(3-chloro-4-fluorophenylamino)-7-methoxy-6-[3-(4-morpholinyl)propoxyl]quinazoline, N-(3-ethynylphenyl)-6,7-bis (2-methoxyethoxy)-4-quinazolinamine, BIBX1382, 2,3,9, 10,11,12-hexahydro-10-(hydroxymethyl)-10-hydroxy-9-methyl-9,12-epoxy-1H-diindolo[1,2,3-fg:3',2',1'-kl]pyrrolo [3,4-i][1,6]benzodiazocin-1-one, SH268, genistein, imatinib (STI571), CEP2563, 4-(3-chlorophenylamino)-5,6-dimethyl-7H-pyrrolo[2,3-d]pyrimidinemethane sulfonate, 4-(3-bromo-4-hydroxyphenyl)amino-6,7-dimethoxyquinazoline, 4-(4'-hydroxyphenyl)amino-6,7-dimethoxyquinazoline, SU6668, STI571A, N-4-chlorophenyl-4-(4-pyridylmethyl)-1-phthalazinamine, and EMD121974.

Combinations with compounds other than anti-cancer compounds are also encompassed in the instant methods. For example, combinations of the instantly claimed compounds with PPAR-γ (i.e., PPAR-gamma) agonists and PPAR-δ (i.e., PPAR-delta) agonists are useful in the treatment of certain malignancies. PPAR-γ and PPAR-δ are the nuclear peroxisome proliferator-activated receptors γ and δ. The expression of PPAR-γ on endothelial cells and its involvement in angiogenesis has been reported in the literature (see *J. Cardiovasc. Pharmacol.* 1998; 31:909-913; *J. Biol. Chem.* 1999; 274:9116-9121; *Invest. Opthalmol. Vis. Sci.* 2000; 41:2309-2317). More recently, PPAR-γ agonists have been shown to inhibit the angiogenic response to VEGF in vitro; both troglitazone and rosiglitazone maleate inhibit the development of retinal neovascularization in mice. (*Arch. Ophthamol.* 2001; 119:709-717). Examples of PPAR-γ agonists and PPAR-γ/α agonists include, but are not limited to, thiazolidinediones (such as DRF2725, CS-011, troglitazone, rosiglitazone, and pioglitazone), fenofibrate, gemfibrozil, clofibrate, GW2570, SB219994, AR-H039242, JTT-501, MCC-555, GW2331, GW409544, NN2344, KRP297, NP0110, DRF4158, NN622, GI262570, PNU182716, DRF552926, 2-[(5,7-dipropyl-3-trifluoromethyl-1,2-benzisoxazol-6-yl)oxy]-2-methylpropionic acid (disclosed in U.S. Ser. No. 09/782,856), and 2(R)-7-(3-(2-chloro-4-(4-fluorophenoxy)phenoxy)propoxy)-2-ethylchromane-2-carboxylic acid (disclosed in U.S. Ser. No. 60/235,708 and 60/244,697).

Another embodiment of the instant invention is the use of the presently disclosed compounds in combination with gene therapy for the treatment of cancer. For an overview of genetic strategies to treating cancer see Hall et al (*Am J Hum Genet.* 61:785-789, 1997) and Kufe et al (*Cancer Medicine,* 5th Ed, pp 876-889, BC Decker, Hamilton 2000). Gene therapy can be used to deliver any tumor suppressing gene. Examples of such genes include, but are not limited to, p53, which can be delivered via recombinant virus-mediated gene transfer (see U.S. Pat. No. 6,069,134, for example), a uPA/uPAR antagonist ("Adenovirus-Mediated Delivery of a uPA/uPAR Antagonist Suppresses Angiogenesis-Dependent Tumor Growth and Dissemination in Mice," *Gene Therapy,* August 1998; 5 (8):1105-13), and interferon gamma (*J Immunol* 2000; 164:217-222).

The compounds of the instant invention may also be administered in combination with an inhibitor of inherent multidrug resistance (MDR), in particular MDR associated with high levels of expression of transporter proteins. Such MDR inhibitors include inhibitors of p-glycoprotein (P-gp), such as LY335979, XR9576, OC144-093, R101922, VX853 and PSC833 (valspodar).

A compound of the present invention may be employed in conjunction with anti-emetic agents to treat nausea or emesis, including acute, delayed, late-phase, and anticipatory emesis, which may result from the use of a compound of the present invention, alone or with radiation therapy. For the prevention or treatment of emesis, a compound of the present invention may be used in conjunction with other anti-emetic agents, especially neurokinin-1 receptor antagonists, 5HT3 receptor antagonists, such as ondansetron, granisetron, tropisetron, and zatisetron, GABAB receptor agonists, such as baclofen, a corticosteroid such as Decadron (dexamethasone), Kenalog, Aristocort, Nasalide, Preferid, Benecorten or others such as disclosed in U.S. Pat. Nos. 2,789,118, 2,990,401, 3,048,581, 3,126,375, 3,929,768, 3,996,359, 3,928,326 and 3,749,712, an antidopaminergic, such as the phenothiazines (for example prochlorperazine, fluphenazine, thioridazine and mesoridazine), metoclopramide or dronabinol. In an embodiment, an anti-emesis agent selected from a neurokinin-1 receptor antagonist, a 5HT3 receptor antagonist and a corticosteroid is administered as an adjuvant for the treatment or prevention of emesis that may result upon administration of the instant compounds.

Neurokinin-1 receptor antagonists of use in conjunction with the compounds of the present invention are fully described, for example, in U.S. Pat. Nos. 5,162,339, 5,232,929, 5,242,930, 5,373,003, 5,387,595, 5,459,270, 5,494,926, 5,496,833, 5,637,699, 5,719,147; European Patent Publication Nos. EP 0 360 390, 0 394 989, 0 428 434, 0 429 366, 0 430 771, 0 436 334, 0 443 132, 0 482 539, 0 498 069, 0 499 313, 0 512 901, 0 512 902, 0 514 273, 0 514 274, 0 514 275, 0 514 276, 0 515 681, 0 517 589, 0 520 555, 0 522 808, 0 528 495, 0 532 456, 0 533 280, 0 536 817, 0 545 478, 0 558 156, 0 577 394, 0 585 913, 0 590 152, 0 599 538, 0 610 793, 0 634 402, 0 686 629, 0 693 489, 0 694 535, 0 699 655, 0 699 674, 0 707 006, 0 708 101, 0 709 375, 0 709 376, 0 714 891, 0 723 959, 0 733 632 and 0 776 893; PCT International Patent Publication Nos. WO 90/05525, 90/05729, 91/09844, 91/18899, 92/01688, 92/06079, 92/12151, 92/15585, 92/17449, 92/20661, 92/20676, 92/21677, 92/22569, 93/00330, 93/00331, 93/01159, 93/01165, 93/01169, 93/01170, 93/06099, 93/09116, 93/10073, 93/14084, 93/14113, 93/18023, 93/19064, 93/21155, 93/21181, 93/23380, 93/24465, 94/00440, 94/01402, 94/02461, 94/02595, 94/03429, 94/03445, 94/04494, 94/04496, 94/05625, 94/07843, 94/08997, 94/10165, 94/10167, 94/10168, 94/10170, 94/11368, 94/13639, 94/13663, 94/14767, 94/15903, 94/19320, 94/19323, 94/20500, 94/26735, 94/26740, 94/29309, 95/02595, 95/04040, 95/04042, 95/06645, 95/07886, 95/07908, 95/08549, 95/11880, 95/14017, 95/15311, 95/16679, 95/17382, 95/18124, 95/18129, 95/19344, 95/20575, 95/21819, 95/22525, 95/23798, 95/26338, 95/28418, 95/30674, 95/30687, 95/33744, 96/05181, 96/05193, 96/05203, 96/06094, 96/07649, 96/10562, 96/16939, 96/18643, 96/20197, 96/21661, 96/29304, 96/29317, 96/29326, 96/29328, 96/31214, 96/32385, 96/37489, 97/01553, 97/01554, 97/03066, 97/08144, 97/14671, 97/17362, 97/18206, 97/19084, 97/19942 and 97/21702; and in British Patent Publication Nos. 2 266 529, 2 268 931, 2 269 170, 2 269 590, 2 271 774, 2 292 144, 2 293 168, 2 293 169, and 2 302 689. The preparation of such compounds is fully described in the aforementioned patents and publications, which are incorporated herein by reference.

In an embodiment, the neurokinin-1 receptor antagonist for use in conjunction with the compounds of the present invention is selected from: 2-(R)-(1-(R)-(3,5-bis(trifluoromethyl)-phenyl)ethoxy)-3-(S)-(4-fluorophenyl)-4-(3-(5-oxo-1H,4H-1,2,4-triazolo)methyl)morpholine, or a pharmaceutically acceptable salt thereof, which is described in U.S. Pat. No. 5,719,147.

A compound of the instant invention may also be useful for treating or preventing cancer, including bone cancer, in combination with bisphosphonates (understood to include bisphosphonates, diphosphonates, bisphosphonic acids and diphosphonic acids). Examples of bisphosphonates include but are not limited to: etidronate (Didronel), pamidronate (Aredia), alendronate (Fosamax), risedronate (Actonel), zoledronate (Zometa), ibandronate (Boniva), incadronate or cimadronate, clodronate, EB-1053, minodronate, neridronate, piridronate and tiludronate including any and all pharmaceutically acceptable salts, derivatives, hydrates and mixtures thereof.

A compound of the instant invention may also be administered with an agent useful in the treatment of anemia. Such an anemia treatment agent is, for example, a continuous eythropoiesis receptor activator (such as epoetin alfa).

A compound of the instant invention may also be administered with an agent useful in the treatment of neutropenia. Such a neutropenia treatment agent is, for example, a hematopoietic growth factor which regulates the production and function of neutrophils such as a human granulocyte colony stimulating factor, (G-CSF). Examples of a G-CSF include filgrastim.

A compound of the instant invention may also be administered with an immunologic-enhancing drug, such as levamisole, isoprinosine and Zadaxin.

A compound of the instant invention may also be useful for treating or preventing cancer, including bone cancer, in combination with bisphosphonates (understood to include bisphosphonates, diphosphonates, bisphosphonic acids and diphosphonic acids). Examples of bisphosphonates include but are not limited to: etidronate (Didronel), pamidronate (Aredia), alendronate (Fosamax), risedronate (Actonel), zoledronate (Zometa), ibandronate (Boniva), incadronate or cimadronate, clodronate, EB-1053, minodronate, neridronate, piridronate and tiludronate including any and all pharmaceutically acceptable salts, derivatives, hydrates and mixtures thereof.

A compound of the instant invention may also be useful for treating or preventing breast cancer in combination with aromatase inhibitors. Examples of aromatase inhibitors include but are not limited to: anastrozole, letrozole and exemestane.

A compound of the instant invention may also be useful for treating or preventing cancer in combination with siRNA therapeutics.

Thus, the scope of the instant invention encompasses the use of the instantly claimed compounds in combination with a second compound selected from: an estrogen receptor modulator, an androgen receptor modulator, retinoid receptor modulator, a cytotoxic/cytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, a PPAR-γ agonist, a PPAR-δ agonist, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, an apoptosis inducing agent, a bisphosphonate, an aromatase inhibitor, an siRNA therapeutic and an agent that interferes with a cell cycle checkpoint.

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents.

As used herein, the term "composition" is intended to encompass a product comprising the specified ingredients in the specified amounts, as well as any product which results, directly or indirectly, from combination of the specified ingredients in the specified amounts.

The term "therapeutically effective amount" as used herein means that amount of active compound or pharmaceutical agent that elicits the biological or medicinal response in a tissue, system, animal or human that is being sought by a researcher, veterinarian, medical doctor or other clinician.

The term "treating cancer" or "treatment of cancer" refers to administration to a mammal afflicted with a cancerous condition and refers to an effect that alleviates the cancerous condition by killing the cancerous cells, but also to an effect that results in the inhibition of growth and/or metastasis of the cancer.

In an embodiment, the angiogenesis inhibitor to be used as the second compound is selected from a tyrosine kinase inhibitor, an inhibitor of epidermal-derived growth factor, an inhibitor of fibroblast-derived growth factor, an inhibitor of platelet derived growth factor, an MMP (matrix metalloprotease) inhibitor, an integrin blocker, interferon-α, interleukin-12, pentosan polysulfate, a cyclooxygenase inhibitor, carboxyamidotriazole, combretastatin A-4, squalamine, 6-O-chloroacetyl-carbonyl)-fumagillol, thalidomide, angiostatin, troponin-1, or an antibody to VEGF. In an embodiment, the estrogen receptor modulator is tamoxifen or raloxifene.

Also included in the scope of the claims is a method of treating cancer that comprises administering a therapeutically effective amount of a compound of Formula I in combination with radiation therapy and/or in combination with a compound selected from: an estrogen receptor modulator, an androgen receptor modulator, retinoid receptor modulator, a cytotoxic/cytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, a PPAR-γ agonist, a PPAR-δ agonist, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, an apoptosis inducing agent, a bisphosphonate, an aromatase inhibitor, an siRNA therapeutic and an agent that interferes with a cell cycle checkpoint.

And yet another embodiment of the invention is a method of treating cancer that comprises administering a therapeutically effective amount of a compound of Formula I in combination with paclitaxel or trastuzumab.

The invention further encompasses a method of treating or preventing cancer that comprises administering a therapeutically effective amount of a compound of Formula I in combination with a COX-2 inhibitor.

The instant invention also includes a pharmaceutical composition useful for treating or preventing cancer that comprises a therapeutically effective amount of a compound of Formula I and a compound selected from: an estrogen receptor modulator, an androgen receptor modulator, a retinoid receptor modulator, a cytotoxic/cytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, a PPAR-γ agonist, a PPAR-δ agonist; an inhibitor of cell proliferation and survival signaling, a bisphosphonate, an aromatase inhibitor, an siRNA therapeutic and an agent that interferes with a cell cycle checkpoint.

These and other aspects of the invention will be apparent from the teachings contained herein.

Assays

The compounds of the instant invention described in the Examples were tested by the assays described below and were found to have MET inhibitory activity. Other assays are known in the literature and could be readily performed by those of skill in the art (see, for example, U.S. Patent Application Publications US 2005/0075340 A1, Apr. 7, 2005, pages 18-19; and PCT Publication WO 2005/028475, Mar. 31, 2005, pages 236-248).

I. In Vitro Kinase Assays

Recombinant GST-tagged cytosolic domains of human c-Met and other receptor tyrosine kinases including mouse c-Met, human Ron, KDR, IGFR, EGFR, FGFR, Mer, TrkA and Tie2 are used to determine whether the compounds of the instant invention modulate the enzymatic activities of these kinases.

Soluble recombinant GST-tagged cytosolic domains of c-Met and other receptor tyrosine kinases are expressed in a baculovirus system (Pharmingen) according to a protocol recommended by the manufacturer. The c-DNA encoding each cytosolic domain is subcloned into a baculovirus expression vector (pGcGBLT-A, B or C, Pharmingen) containing an in frame 6× histidine tag and a GST tag. The resulting plasmid construct and BaculoGold baculovirus DNA (Pharmingen) are used to co-transfect Sf9 or Sf21 insect cells. After confirming expression of GST-tagged kinase fusion, a high titer recombinant baculovirus stock is produced, expression conditions are optimized, and a scaled up expression of rat KDR-GST fusion is performed. The fusion kinase is then purified from the insect cell lysate by affinity chromatography using glutathione agarose (Pharmingen). The purified protein is dialyzed against 50% glycerol, 2 mM DTT, 50 mM Tris-HCl (pH 7.4) and stored at −20° C. The protein concentrations of the fusion proteins are determined using Coomassie Plus Protein Assay (Pierce) with BSA as standard.

The kinase activities of c-Met and other kinases are measured using a modified version of the homogeneous time-resolved tyrosine kinase assay described by Park et al. (1999, *Anal. Biochem.* 269:94-104).

The procedure for determining the potency of a compound to inhibit c-Met kinase comprises the following steps:

1. Prepare 3-fold serial diluted compound solutions in 100% dimethyl sulfoxide (DMSO) at 20× of the desired final concentrations in a 96 well plate.
2. Prepare a master reaction mix containing 6.67 mM $MgCl_2$, 133.3 mM NaCl, 66.7 mM Tris-HCl (pH 7.4), 0.13 mg/ml BSA, 2.67 mM dithiothreitol, 0.27 nM recombinant c-Met and 666.7 nM biotinylated synthetic peptide substrate (biotin-ahx-EQEDEPEGDYFEWLE-$CONH_2$) (SEQ. ID. NO.:1).
3. In a black assay plate, add 2.5 µl of compound solution (or DMSO) and 37.5 µl of master reaction mix per well. Initiate the kinase reaction by adding 10 µl of 0.25 mM MgATP per well. Allow the reactions to proceed for 80 min at room temperature. The final conditions for the reaction are 0.2 nM c-Met, 0.5 µM substrate, 50 µM MgATP, 5 mM $MgCl_2$, 100 mM NaCl, 2 mM DTT, 0.1 mg/ml BSA, 50 mM Tris (pH 7.4) and 5% DMSO.
4. Stop the kinase reaction with 50 µl of Stop/Detection buffer containing 10 mM EDTA, 25 mM HEPES, 0.1% TRITON X-100, 0.126 µg/ml Eu-chelate labeled anti-phosphotyrosine antibody PY20 (cat. #AD0067, PerkinElmer) and 45 µg/ml Streptavidin-allophycocyanin conjugate (cat. #PJ25S, Prozyme).
5. Read HTRF signals on a Victor reader (PerkinElmer) in HTRF mode after 60 min.
6. $IC_{50}$ is determined by fitting the observed relationship between compound concentration and HTRF signal with a 4-parameter logistic equation.

Essentially the same procedure was used to determine the potency of compounds to inhibit mouse c-Met, human Ron, KDR, IGFR, EGFR, FGFR, Mer, TrkA and Tie2 except that the concentration of enzyme varied in individual assays (0.2 nM mouse c-Met; 2.5 nM Ron, 8 nM KDR; 0.24 nM IGFR; 0.24 nM EGFR; 0.14 nM FGFR; 16 nM Mer; 8 nM TrkA; 8 nM Tie2).

The compounds 1 to 235 in the Examples were tested in the above assay and found to have an $IC_{50} \leq 50$ µM.

II. Cell Based-c-Met Autophosphrylation Assay

A sandwich ELISA assay is used to assess MET autophosphorylation in MKN45 gastric cancer cells, in which MET is constitutively activated. Briefly a monolayer of cells was pre-treated with compounds or the vehicle and then lysed. The MET in a cell lysate was captured by an anti-MET antibody immobilized on a plastic surface. A generic anti-phosphotyrosine antibody or one of several specific anti-phospho-MET antibodies is then allowed to bind captured MET and is detected using HRP-conjugated secondary antibody.

The procedure for determining the potency of a compound to inhibit MET autophosphorylation in MKN45 cells comprises the following steps:

Day 1

1. Coat a 96-well ELISA plate overnight at 4° C. with 100 µl/well of 1 µg/ml capture antibody solution (Af276, R&D).
2. Seed a separate 96-well culture plate with MKN45 cells at 90,000 cells/well in 0.1 ml of growth media (RPMI 1640, 10% FBS, 100 ug/mL Pen-Strep, 100 ug/mL L-glutamine, and 10 mM HEPES) and culture overnight at 37° C./5% $CO_2$ to 80-90% confluence.

Day 2

1. Wash the ELISA plate 4× with 200 µl/well of wash buffer (TBST+0.25% BSA). Incubate the ELISA plate with 200 µl/well of blocking buffer (TBST+1.5% BSA) for 3-5 hrs at RT.
2. Prepare a half-long dilution series of 200× compound in DMSO. Dilute the series to 10× with assay media (RPMI 1640, 10% FBS, and 10 mM HEPES).
3. Add 10× compound solutions (11 µl/well) to the culture plate containing MKN45 cells. Incubate the plate at 37° C./5% $CO_2$ for 60 min.
4. Lyse the cells with 100 µl/well of lysis buffer (30 mM Tris, pH 7.5, 5 mM EDTA, 50 mM NaCl, 30 mM sodium pyrophosphate, 50 mM NaF, 0.5 mM $Na_3VO_4$, 0.25 mM potassium bisperoxo(1,10-phenanthroline)-oxovanadate, 0.5% NP40, 1% Triton X-100, 10% glycerol, and a protease inhibitor cocktail) at 4° C. for 90 min.
5. Remove blocking buffer from the ELISA plate, wash the plate 4× with 200 µl/well of wash buffer. Transfer 90 µl/well of MKN45 cell lysate from the culture plate to the ELISA plate. Incubate sealed assay plate at 4° C. with gentle shaking overnight.

Day 3

1. Wash the ELISA plates 4 times with 200 µl/well wash buffer.
2. Incubate with 100 µl/well primary detection antibody (1 µg/ml in TBST+1% BSA) for 1.5 hours at ambient temperature. The following primary antibodies have been used: 4G10 from UpState, anti-pMet (1349) and anti-pMet (1369), both from Biosource.
3. Wash the ELISA plates 4 times with wash buffer. Add 100 µl/well of secondary antibody (1:1000 anti-mouse IgG-HRP diluted in TBST+1% BSA for 4G10, or 1:1000 anti-rabbit IgG-HRP for anti-pMet (1349) and anti-pMet (1365)). Incubate at room temperature with gentle mixing for 1.5 hours. Wash 4× with 200 ul/well wash buffer.
4. Add 100 μl/well of Quanta Blu reagent (Pierce) and incubate at room temperature for 8 minutes. Read fluorescence (Excitation wavelength: 314 nm, emission wavelength: 425 nm) on a Spectramax Gemini EM plate reader (Molecular Devices).
5. $IC_{50}$ is calculated by fitting the relationship between compound concentration and fluorescence signal with a 4-parameter logistic equation.

III. MKN45 Cell Proliferation/Viability Assay

MKN45 human gastric cancer cells are known to over-express constitutively activated c-met. siRNA-mediated partial knock down of c-Met was found to induce pronounced growth inhibition and apoptosis in MKN45 cells, suggesting a vital role of c-Met in this cell line. The assay described here measures the effect of c-Met inhibitors on proliferation/viability of MKN45 cells. The procedure for determining the potency of a compound to inhibit MKN45 proliferation/viability comprises the following steps.

On day 1, plate MKN45 cells at 3000 cells/95 μl medium (RPMI/10% FCS, 100 mM HEPES, penicillin and streptomycin) per well in a 96 well plate. Maintain the plate in an incubator at 37° C./5% $CO_2$. Prepare 3-fold serial diluted compound solutions at 1000× of desired final concentrations in DMSO.

On day 2, prepare 50× compound solutions by diluting the 1000× compound solutions with the medium. Add 5 μl 20× compound solution per well to the MKN45 cell culture described above. Return the plate to the incubator.

On day 5, add 50 μl lysis buffer (ViaLight Reagents Kit, Catalog No. LT07-221, Cambrex): per well. Lyse the cells at room temperature for 15 minutes. Then add 50 μl detection reagent (ViaLight Reagents Kit) and incubate for 3 minutes. The plate is read on a TOPCOUNT (PerkinElmer) in luminescence mode. $IC_{50}$ is calculated by fitting the relationship between compound concentration and luminescence signal with a 4-parameter logistic equation.

IV. HGF-Induced Cell Migration Assay

The HGF-induced migration of HPAF pancreatic cancer cells was assessed using BD Falcon Fluoroblock 96-Multiwell Insert plates (Cat #351164, BD Discovery Labware). The plate consists of wells each of which is partitioned by a micro-porous membrane into the top and bottom chambers. Pancreatic cancer cells are plated on the top side of the membrane and migrate to the underside of the membrane in response to chemo-attractant added to the lower chamber. The cells on the under side of the membrane are labeled with a fluorescent dye and detected by a fluorescence plate reader. The procedure for determining the potency of a compound to inhibit cell migration comprises the following steps.
1. Prepare test compound solutions of 1000× final concentrations in 100% DMSO
2. Dilute the above solutions 50× with DMEM/10% FCS to obtain compound solutions 20× of the final concentrations.
3. Fill each lower chamber of a Fluoroblock 96-Muntiwell Insert plate with 180 μl DMEM/10% FCS, and plate 8,000 HPAF pancreatic cancer cells in 50 ul DMEM/10% FCS in each upper chamber.
4. 1-2 hours after plating, add 2.5 μl and 10 μl of a 20× compound solution to the upper and the lower chamber respectively. Incubate the plate at 37° C. for 60 min, and then add concentrated HGF to lower chamber to a final HGF concentration of 15 ng/ml. The insert plates are incubated overnight for 20 hours.
5. An aliquot of a concentrated Calcein dye (Molecular Probes) is added to each lower chamber to give 5 μg/ml final dye concentration and the cells are labeled for 1 hour. Wash each lower chamber with 200 μl DMEM/10% FCS
6. Read fluorescence on a Victor reader (PerkinElmer) in bottom read mode (Excitation wave length: 485 nm, emission wavelength: 535 nm).
7. $IC_{50}$ is calculated by fitting the relationship between compound concentration and fluorescence signal with a 4-parameter logistic equation.

EXAMPLES

Examples provided are intended to assist in a further understanding of the invention. Particular materials employed, species and conditions are intended to be illustrative of the invention and not limiting of the reasonable scope thereof.

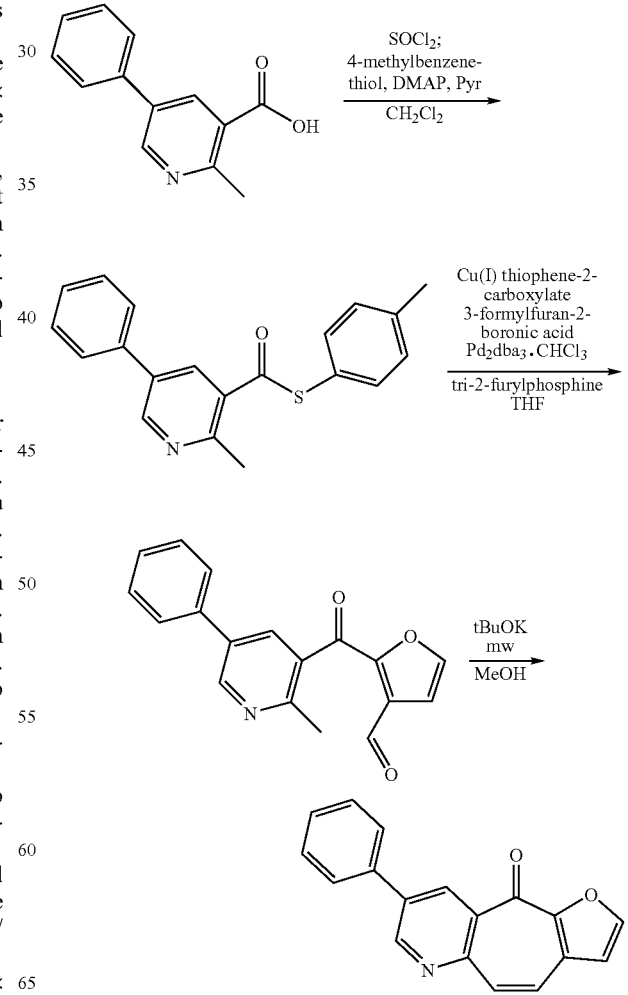

Scheme 1

Example 1

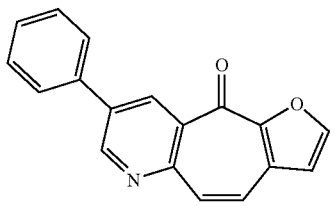

Step 1: (4-methylphenyl) 2-methyl-5-phenylpyridine-3-carbothioate

A mixture of 3-carboxy-2-methyl-5-phenylpyridinium chloride (Marcoux, J.; Marcotte, F.-A.; Wu, J.; Dormer, P. G.; Davies, I. W.; Hughes, D.; Reider, P. J., *J. Org. Chem.*, 2001, 66, 4194. 200 mg, 0.80 mmol) and $SOCl_2$ (1 mL) was heated to 80° C. for 45 min, cooled to room temperature, and concentrated. The residue was dissolved in $CH_2Cl_2$ (4 mL) and cooled to 0° C. 4-metyylbenzenetiol (120 mg, 0.97 mmol) and DMAP (20 mg, 0.16 mmol) were added to the mixture, and then pyridine (0.16 mL, 2.0 mmol) was added over 20 min. The reaction mixture was allowed to warm to room temperature, and left to stir overnight. The mixture was concentrated and purified by prep-HPLC to afford the title compound. $^1$H NMR (600 MHz, $CDCl_3$) δ 8.85 (d, 1H); 8.34 (d, 1H); 7.63 (d, 2H); 7.51 (t, 2H); 7.44 (t, 1H); 7.41 (d, 2H); 7.29 (d, 2H); 2.75 (s, 3H); 2.41 (s, 3H). LRMS (ESI) calc'd for $C_{20}H_{17}NOS$ [M+H]$^+$, 320.1. found 320.1.

Step 2: 2-[(2-methyl-5-phenylpyridin-3-yl)carbonyl]-3-furaldehyde

To a mixture of S-(4-methylphenyl) 2-methyl-5-phenylpyridine-3-carbothioate (66 mg, 0.20 mmol), Cu(I) thiophene-2-carboxylate (59 mg, 0.31 mmol), 3-formylfuran-2-boronic acid (31 mg, 0.22 mmol), $Pd_2dba_3.CHCl_3$ (2 mg, 0.002 mmol), and tri-2-furylphosphine (1.4 mg, 0.006 mmol) was added THF (2.5 mL). The reaction mixture was heated to 50° C. for 15 h, cooled to room temperature, diluted with EtOAc, and washed with 1 N HCl and brine. The organic layer was concentrated and purified by flash chromatography to afford the title compound. $^1$H NMR (600 MHz, $CDCl_3$) δ 10.60 (s, 1H); 8.91 (s, 1H); 8.02 (s, 1H); 7.40-7.61 (series of m, 6H); 7.05 (s, 1H); 2.66 (s, 3H). LRMS (ESI) calc'd for $C_{18}H_{13}NO_3$ [M+H]$^+$, 292.1. found 292.1.

Step 3: 8-phenyl-10H-furo[2',3':4,5]cyclohepta[1,2-b]pyridin-10-one (Compound 1)

To 2-[(2-methyl-5-phenylpyridin-3-yl)carbonyl]-3-furaldehyde (3.4 mg, 0.011 mmol) in MeOH (0.4 mL) was added tBuOK (1 M in THF, 13 uL, 0.013 mmol). The reaction mixture was heated to 100° C. under microwave for 10 min and 160° C. for 20 min. The mixture was purified by prep-HPLC to afford the title compound as the TFA salt. $^1$H NMR (600 MHz, $CD_3OD$) δ 9.39 (d, 1H); 9.37 (d, 1H); 8.17 (d, 1H); 7.87 (d, 2H); 7.80 (d, 1H); 7.58 (m, 3H); 7.50 (t, 1H); 7.11 (d, 1H). LRMS (ESI) calc'd for $C_{18}H_{11}NO_2$ [M+H]$^+$, 274.1. found 274.1.

The following compounds were made according to Scheme 5.

| Compound number | Structure | Name | MS |
|---|---|---|---|
| 2 | 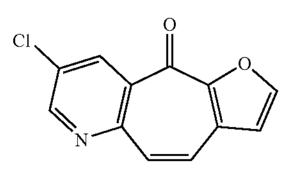 | 8-chloro-10H-furo[2',3':4,5]cyclohepta[1,2-b]pyridin-10-one | calc'd (M + H)$^+$ 232.0; found (M + H)$^+$ 231.7 |
| 3 | 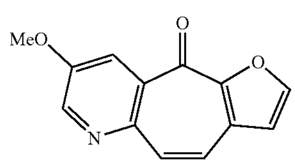 | 8-methoxy-10H-furo[2',3':4,5]cyclohepta[1,2-b]pyridin-10-one | calc'd (M + H)$^+$ 228.1; found (M + H)$^+$ 227.8 |
| 4 | 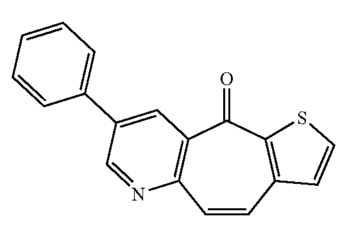 | 8-phenyl-10H-thieno[2',3':4,5]cyclohepta[1,2-b]pyridin-10-one, isolated as the TFA salt | calc'd (M + H)$^+$ 290.1; found (M + H)$^+$ 289.8 |

-continued

| Compound number | Structure | Name | MS |
|---|---|---|---|
| 5 | 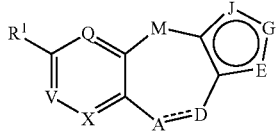 | 6-phenyl-4H-thieno[2',3':4,5]cyclohepta[1,2-b]pyridin-4-one, isolated as the TFA salt | calc'd (M + H)$^+$ 290.1; found (M + H)$^+$ 289.8 |

What is claimed is:

1. A compound of Formula I:

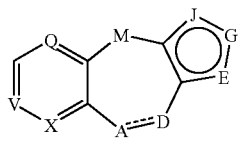

I or pharmaceutically acceptable salts or stereoisomers thereof, wherein:

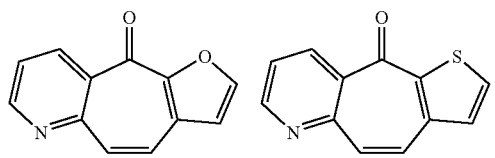

is selected from

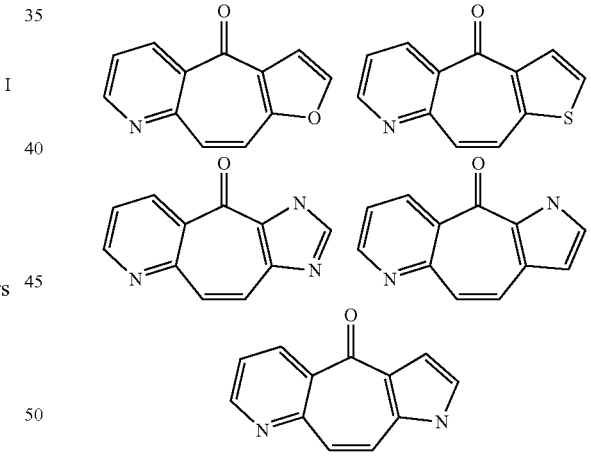

a is independently 0 or 1;
b is independently 0 or 1;
m is independently 0, 1, or 2;

$R^1$ is selected from halogen, aryl, heterocyclic, $C_{1-6}$alkyl, —O—$C_{1-6}$alkyl and $NR^{10}R^{11}$; said alkyl, aryl and heterocyclic group optionally substituted with one to five substituents, each substituent independently selected from $R^8$;

$R^2$ and $R^3$ are independently selected from hydrogen, OH, —O—$C_{1-6}$alkyl, —O—C(=O)$C_{1-6}$alkyl, —O-aryl and $NR^{10}R^{11}$, each alkyl and aryl optionally substituted with one to five substituents, each substituent independently selected from $R^8$;

$R^4$ and $R^5$ are each independently selected from hydrogen, $C_{1-6}$alkyl, OH, —O—$C_{1-6}$alkyl, —O—C(=O)$C_{1-6}$ alkyl, —O-aryl, S(O)$_m R^a$ and $NR^{10}R^{11}$, each alkyl and aryl optionally substituted with one to five substituents, each substituent independently selected from $R^8$;

$R^6$ is selected from hydrogen, $C_{1-6}$alkyl, $C_{2-6}$ alkenyl, $C_{2-6}$ alkynyl, OH, —O—$C_{1-6}$alkyl, —O—C(=O)$C_{1-6}$ alkyl, —O-aryl, S(O)$_m R^a$, —C(=O)$NR^{10}R^{11}$, —NHS(O)$_2 NR^{10}R^{11}$ and $NR^{10}R^{11}$, each alkyl, alkenyl, alkynyl and aryl optionally substituted with one to five substituents, each substituent independently selected from $R^8$;

$R^8$ independently is:
1) (C=O)$_a$O$_b$C$_1$-C$_{10}$ alkyl,
2) (C=O)$_a$O$_b$aryl,
3) C$_2$-C$_{10}$ alkenyl,
4) C$_2$-C$_{10}$ alkynyl,
5) (C=O)$_a$O$_b$ heterocyclyl,
6) CO$_2$H,
7) halo,
8) CN,
9) OH,
10) O$_b$C$_1$-C$_6$ perfluoroalkyl,
11) O$_a$(C=O)$_b$NR$^{10}$R$^{11}$,
12) S(O)$_m$R$^a$,
13) S(O)$_2$NR$^{10}$R$^{11}$,
14) OS(=O)R$^a$,
15) oxo,
16) CHO,
17) (N=O)R$^{10}$R$^{11}$,
18) (C=O)$_a$O$_b$C$_3$-C$_8$ cycloalkyl,
19) O$_b$SiR$^a_3$, or
20) NO$_2$;

said alkyl, aryl, alkenyl, alkynyl, heterocyclyl, and cycloalkyl optionally substituted with one, two or three substituents selected from $R^9$;

two $R^8$s, attached to the same carbon atom are combined to form —(CH$_2$)$_u$— wherein u is 3 to 6 and one or two of the carbon atoms is optionally replaced by a moiety selected from O, S(O)$_m$, —N(R$^a$)C(O)—, —N(R$^b$)— and —N(COR$^a$)—;

$R^9$ is independently selected from:
1) (C=O)$_a$O$_b$(C$_1$-C$_{10}$)alkyl,
2) O$_b$(C$_1$-C$_3$)perfluoroalkyl,
3) oxo,
4) OH,
5) halo,
6) CN,
7) (C$_2$-C$_{10}$)alkenyl,
8) (C$_2$-C$_{10}$)alkynyl,
9) (C=O)$_a$O$_b$(C$_3$-C$_6$)cycloalkyl,
10) (C=O)$_a$O$_b$(C$_0$-C$_6$)alkylene-aryl,
11) (C=O)$_a$O$_b$(C$_0$-C$_6$)alkylene-heterocyclyl,
12) (C=O)$_a$O$_b$(C$_0$-C$_6$)alkylene-N(R$^b$)$_2$,
13) C(O)R$^a$,
14) (C$_0$-C$_6$)alkylene-CO$_2$R$^a$,
15) C(O)H,
16) (C$_0$-C$_6$)alkylene-CO$_2$H,
17) C(O)N(R$^b$)$_2$,
18) S(O)$_m$R$^a$, and
19) S(O)$_2$NR$^{10}$R$^{11}$;

said alkyl, alkenyl, alkynyl, cycloalkyl, aryl, and heterocyclyl is optionally substituted with one, two or three substituents selected from R$^b$, OH, (C$_1$-C$_6$)alkoxy, halogen, CO$_2$H, CN, O(C=O)C$_1$-C$_6$ alkyl, oxo, and N(R$^b$)$_2$; or two $R^9$s, attached to the same carbon atom are combined to form —(CH$_2$)$_u$— wherein u is 3 to 6 and one or two of the carbon atoms is optionally replaced by a moiety selected from O, S(O)$_m$, —N(R$^a$)C(O)—, —N(R$^b$)— and —N(COR$^a$)—;

$R^{10}$ and $R^{11}$ are independently selected from:
1) H,
2) (C=O)O$_b$C$_1$-C$_{10}$ alkyl,
3) (C=O)O$_b$C$_3$-C$_8$ cycloalkyl,
4) (C=O)O$_b$aryl,
5) (C=O)O$_b$ heterocyclyl,
6) C$_1$-C$_{10}$ alkyl,
7) aryl,
8) C$_2$-C$_{10}$ alkenyl,
9) C$_2$-C$_{10}$ alkynyl,
10) heterocyclyl,
11) C$_3$-C$_8$ cycloalkyl,
12) SO$_2$R$^a$, and
13) (C=O)NR$^b_2$, said alkyl, cycloalkyl, aryl, heterocyclyl, alkenyl, and alkynyl is optionally substituted with one, two or three substituents selected from $R^8$, or $R^{10}$ and $R^{11}$ can be taken together with the nitrogen to which they are attached to form a monocyclic or bicyclic heterocycle with 5-7 members in each ring and optionally containing, in addition to the nitrogen, one or two additional heteroatoms selected from N, O and S, said monocyclic or bicyclic heterocycle optionally substituted with one, two or three substituents selected from $R^9$;

$R^a$ is independently selected from: (C$_1$-C$_6$)alkyl, (C$_2$-C$_6$)alkenyl, (C$_3$-C$_6$)cycloalkyl, aryl, —(C$_1$-C$_6$)alkylene-aryl, heterocyclyl and —(C$_1$-C$_6$)alkyleneheterocyclyl;

$R^b$ is independently selected from: H, (C$_1$-C$_6$)alkyl, aryl, —(C$_1$-C$_6$)alkylenearyl, heterocyclyl, —(C$_1$-C$_6$)alkyleneheterocyclyl, (C$_3$-C$_6$)cycloalkyl, (C=O)OC$_1$-C$_6$ alkyl, (C=O)C$_1$-C$_6$ alkyl or S(O)$_2$R$^a$; and $R^c$ is independently selected from: H, (C$_1$-C$_6$)alkyl, (C$_2$-C$_6$)alkenyl, (C$_3$-C$_6$)cycloalkyl, aryl, —(C$_1$-C$_6$)alkylenearyl, heterocyclyl and —(C$_1$-C$_6$)alkyleneheterocyclyl; and heterocyclyl is a 3- to 10-membered aromatic or nonaromatic heterocycle containing from 1 to 4 heteroatoms selected from the group consisting of O, N and S, and includes bicyclic groups and wherein attachment of a heterocyclyl substituent can occur via a carbon atom or via a heteroatom.

2. The compound according to claim 1 of the Formula II:

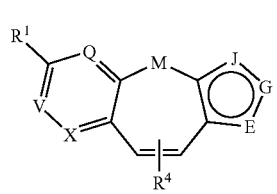

or pharmaceutically acceptable salts or stereoisomers thereof, wherein:

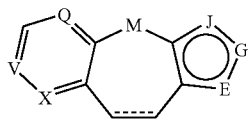

is selected from

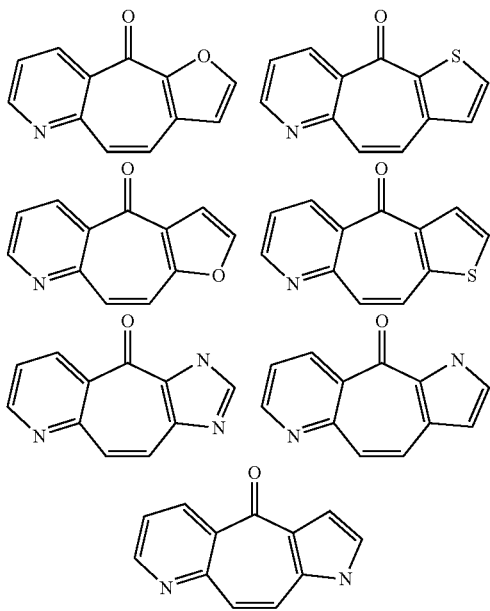

a is independently 0 or 1;
b is independently 0 or 1;
m is independently 0, 1, or 2;
R$^1$ is selected from halogen, aryl, heterocyclic, —O—C$_{1-6}$alkyl and NR$^{10}$R$^{11}$; said alkyl, aryl and heterocyclic group optionally substituted with one to five substituents, each substituent independently selected from R$^8$;
R$^2$ and R$^3$ are independently selected from hydrogen, OH, —O—C$_{1-6}$ alkyl, —O—C(=O)C$_{1-6}$ alkyl, —O-aryl and NR$^{10}$R$^{11}$, each alkyl and aryl optionally substituted with one to five substituents, each substituent independently selected from R$^8$;
R$^4$ is selected from: hydrogen, C$_{1-6}$alkyl, OH, NO$_2$, —O—C$_{1-6}$alkyl, —O—C(=O)C$_{1-6}$ alkyl, —O-aryl, S(O)$_m$R$^a$ and NR$^{10}$R$^{11}$, each alkyl and aryl optionally substituted with one to five substituents, each substituent independently selected from R$^8$;
R$^6$ is selected from hydrogen, C$_{1-6}$alkyl, C$_{2-6}$ alkenyl, C$_{2-6}$ alkynyl, OH, —O—C$_{1-6}$alkyl, —O—C(=O) C$_{1-6}$ alkyl, —O-aryl, S(O)$_m$R$^a$, —C(=O)NR$^{10}$R$^{11}$, —NHS(O)$_2$NR$^{10}$R$^{11}$ and NR$^{10}$R$^{11}$, each alkyl, alkenyl, alkynyl and aryl optionally substituted with one to five substituents, each substituent independently selected from R$^8$;
R$^8$ independently is:
1) (C=O)$_a$O$_b$C$_1$-C$_{10}$ alkyl,
2) (C=O)$_a$O$_b$aryl,
3) C$_2$-C$_{10}$ alkenyl,
4) C$_2$-C$_{10}$ alkynyl,
5) (C=O)$_a$O$_b$ heterocyclyl,
6) CO$_2$H,
7) halo,
8) CN,
9) OH,
10) O$_b$C$_1$-C$_6$ perfluoroalkyl,
11) O$_a$(C=O)$_b$NR$^{10}$R$^{11}$,
12) S(O)$_m$R$^a$,
13) S(O)$_2$NR$^{10}$R$^{11}$,
14) OS(=O)R$^a$,
15) oxo,
16) CHO,
17) (N=O)R$^{10}$R$^{11}$,
18) (C=O)$_a$O$_b$C$_3$-C$_8$ cycloalkyl,
19) O$_b$SiR$^a$$_3$, or
20) NO$_2$;
said alkyl, aryl, alkenyl, alkynyl, heterocyclyl, and cycloalkyl optionally substituted with one, two or three substituents selected from R$^9$;
two R$^8$s, attached to the same carbon atom are combined to form —(CH$_2$)$_u$— wherein u is 3 to 6 and one or two of the carbon atoms is optionally replaced by a moiety selected from O, S(O)$_m$, —N(R$^a$)C(O)—, —N(R$^b$)— and —N(COR$^a$)—;
R$^9$ is independently selected from:
1) (C=O)$_a$O$_b$(C$_1$-C$_{10}$)alkyl,
2) O$_b$(C$_1$-C$_3$)perfluoroalkyl,
3) oxo,
4) OH,
5) halo,
6) CN,
7) (C$_2$-C$_{10}$)alkenyl,
8) (C$_2$-C$_{10}$)alkynyl,
9) (C=O)$_a$O$_b$(C$_3$-C$_6$)cycloalkyl,
10) (C=O)$_a$O$_b$(C$_0$-C$_6$)alkylene-aryl,
11) (C=O)$_a$O$_b$(C$_0$-C$_6$)alkylene-heterocyclyl,
12) (C=O)$_a$O$_b$(C$_0$-C$_6$)alkylene-N(R$^b$)$_2$,
13) C(O)R$^a$,
14) (C$_0$-C$_6$)alkylene-CO$_2$R$^a$;
15) C(O)H,
16) (C$_0$-C$_6$)alkylene-CO$_2$H,
17) C(O)N(R$^b$)$_2$,
18) S(O)$_m$R$^a$, and
19) S(O)$_2$NR$^{10}$R$^{11}$;
said alkyl, alkenyl, alkynyl, cycloalkyl, aryl, and heterocyclyl is optionally substituted with one, two or three substituents selected from R$^b$, OH, (C$_1$-C$_6$)alkoxy, halogen, CO$_2$H, CN, O(C=O)C$_1$-C$_6$ alkyl, oxo, and N(R$^b$)$_2$; or
two R$^9$s, attached to the same carbon atom are combined to form —(CH$_2$)$_u$— wherein u is 3 to 6 and one or two of the carbon atoms is optionally replaced by a moiety selected from O, S(O)$_m$, —N(R$^a$)C(O)—, —N(R$^b$)— and —N(COR$^a$)—;
R$^{10}$ and R$^{11}$ are independently selected from:
1) H,
2) (C=O)O$_b$C$_1$-C$_{10}$ alkyl,
3) (C=O)O$_b$C$_3$-C$_8$ cycloalkyl,
4) (C=O)O$_b$aryl,
5) (C=O)O$_b$heterocyclyl,
6) C$_1$-C$_{10}$ alkyl,
7) aryl,
8) C$_2$-C$_{10}$ alkenyl,
9) C$_2$-C$_{10}$ alkynyl,
10) heterocyclyl,
11) C$_3$-C$_9$ cycloalkyl,
12) SO$_2$R$^a$, and
13) (C=O)NR$^b$$_2$, said alkyl, cycloalkyl, aryl, heterocylyl, alkenyl, and alkynyl is optionally substituted with one, two or three substituents selected from $R^8$, or $R^{10}$ and $R^{11}$ can be taken together with the nitrogen to which they are attached to form a monocyclic or bicyclic heterocycle with 5-7 members in each ring and optionally containing, in addition to the nitrogen, one or two additional heteroatoms selected from N, O and S, said monocyclic or bicyclic heterocycle optionally substituted with one, two or three substituents selected from $R^9$;

$R^a$ is independently selected from: $(C_1\text{-}C_6)$alkyl, $(C_2\text{-}C_6)$alkenyl, $(C_3\text{-}C_6)$cycloalkyl, aryl, —$(C_1\text{-}C_6)$alkylenearyl, heterocyclyl and —$(C_1\text{-}C_6)$alkyleneheterocyclyl;

$R^b$ is independently selected from: H, $(C_1\text{-}C_6)$alkyl, aryl, —$(C_1\text{-}C_6)$alkylenearyl, heterocyclyl, —$(C_1\text{-}C_6)$alkyleneheterocyclyl, $(C_3\text{-}C_6)$cycloalkyl, $(C=O)OC_1\text{-}C_6$ alkyl, $(C=O)C_1\text{-}C_6$ alkyl or $S(O)_2R^a$; and $R^c$ is independently selected from: H, $(C_1\text{-}C_6)$alkyl, $(C_2\text{-}C_6)$alkenyl, $(C_3\text{-}C_6)$cycloalkyl, aryl, —$(C_1\text{-}C_6)$alkylenearyl, heterocyclyl and —$(C_1\text{-}C_6)$alkyleneheterocyclyl.

3. The compound according to claim 2 of the Formula III:

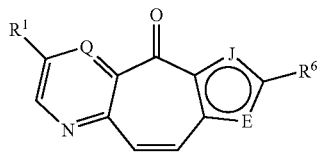

III or pharmaceutically acceptable salts thereof, wherein:

E and J are independently selected from: O, S, —$NR^{10}$— and —$CR^6$—; provided at least one of E and J are not —$CR^6$—, Q is selected from: N and —$CR^8$—;

a is independently 0 or 1;

b is independently 0 or 1;

m is independently 0, 1, or 2;

$R^1$ is selected from halogen, aryl, heterocyclic, and $NR^{10}R^{11}$; said aryl and heterocyclic group optionally substituted with one to five substituents, each substituent independently selected from $R^8$;

$R^6$ is selected from hydrogen, halogen, $C_{1\text{-}6}$alkyl, $C_{2\text{-}6}$ alkenyl, $C_{2\text{-}6}$ alkynyl, OH, —O—$C_1\text{-}C_6$alkyl, —O—C(=O)$C_1\text{-}C_6$ alkyl, —O-aryl, $S(O)_mR^a$ and $NR^{10}R^{11}$, each alkyl and aryl optionally substituted with one to five substituents, each substituent independently selected from $R^8$;

$R^8$ independently is:
1) $(C=O)_aO_bC_1\text{-}C_{10}$ alkyl,
2) $(C=O)_aO_b$aryl,
3) $C_2\text{-}C_{10}$ alkenyl,
4) $C_2\text{-}C_{10}$ alkynyl,
5) $(C=O)_aO_b$ heterocyclyl,
6) $CO_2H$,
7) halo,
8) CN,
9) OH,
10) $O_bC_1\text{-}C_6$ perfluoroalkyl,
11) $O_a(C=O)_bNR^{10}R^{11}$,
12) $S(O)_mR^a$,
13) $S(O)_2NR^{10}R^{11}$,
14) $OS(=O)R^a$,
15) oxo,
16) CHO,
17) $(N=O)R^{10}R^{11}$,
18) $(C=O)_aO_bC_3\text{-}C_8$ cycloalkyl,
19) $O_bSiR^a_3$, or
20) $NO_2$;

said alkyl, aryl, alkenyl, alkynyl, heterocyclyl, and cycloalkyl optionally substituted with one, two or three substituents selected from $R^9$;

two $R^8$s, attached to the same carbon atom are combined to form —$(CH_2)_u$— wherein u is 3 to 6 and one or two of the carbon atoms is optionally replaced by a moiety selected from O, $S(O)_m$, —$N(R^a)C(O)$—, —$N(R^b)$— and —$N(COR^a)$—;

$R^9$ is independently selected from:
1) $(C=O)_aO_b(C_1\text{-}C_{10})$alkyl,
2) $O_b(C_1\text{-}C_3)$perfluoroalkyl,
3) oxo,
4) OH,
5) halo,
6) CN,
7) $(C_2\text{-}C_{10})$alkenyl,
8) $(C_2\text{-}C_{10})$alkynyl,
9) $(C=O)_aO_b(C_3\text{-}C_6)$cycloalkyl,
10) $(C=O)_aO_b(C_0\text{-}C_6)$alkylene-aryl,
11) $(C=O)_aO_b(C_0\text{-}C_6)$alkylene-heterocyclyl,
12) $(C=O)_aO_b(C_0\text{-}C_6)$alkylene-$N(R^b)_2$,
13) $C(O)R^a$,
14) $(C_0\text{-}C_6)$alkylene-$CO_2R^a$,
15) $C(O)H$,
16) $(C_0\text{-}C_6)$alkylene-$CO_2H$,
17) $C(O)N(R^b)_2$,
18) $S(O)_mR^a$, and
19) $S(O)_2NR^{10}R^{11}$;

said alkyl, alkenyl, alkynyl, cycloalkyl, aryl, and heterocyclyl is optionally substituted with one, two or three substituents selected from $R^b$, OH, $(C_1\text{-}C_6)$alkoxy, halogen, $CO_2H$, CN, $O(C=O)C_1\text{-}C_6$ alkyl, oxo, and $N(R^b)_2$; or two $R^9$s, attached to the same carbon atom are combined to form —$(CH_2)_u$— wherein u is 3 to 6 and one or two of the carbon atoms is optionally replaced by a moiety selected from O, $S(O)_m$, —$N(R^a)C(O)$—, —$N(R^b)$— and —$N(COR^a)$—;

$R^{10}$ and $R^{11}$ are independently selected from:
1) H,
2) $(C=O)O_bC_1\text{-}C_{10}$ alkyl,
3) $(C=O)O_bC_3\text{-}C_8$ cycloalkyl,
4) $(C=O)O_b$aryl,
5) $(C=O)O_b$heterocyclyl,
6) $C_1\text{-}C_{10}$ alkyl,
7) aryl,
8) $C_2\text{-}C_{10}$ alkenyl,
9) $C_2\text{-}C_{10}$alkynyl,
10) heterocyclyl,
11) $C_3\text{-}C_8$ cycloalkyl,
12) $SO_2R^a$, and
13) $(C=O)NR^b_2$, said alkyl, cycloalkyl, aryl, heterocylyl, alkenyl, and alkynyl is optionally substituted with one, two or three substituents selected from $R^8$, or $R^{10}$ and $R^{11}$ can be taken together with the nitrogen to which they are attached to form a monocyclic or bicyclic heterocycle with 5-7 members in each ring and optionally containing, in addition to the nitrogen, one or two additional heteroatoms selected from N, O and S, said monocyclic or bicyclic heterocycle optionally substituted with one, two or three substituents selected from $R^9$;

$R^a$ is independently selected from: $(C_1\text{-}C_6)$alkyl, $(C_2\text{-}C_6)$alkenyl, $(C_3\text{-}C_6)$cycloalkyl, aryl, —$(C_1\text{-}C_6)$alkylenearyl, heterocyclyl and —$(C_1\text{-}C_6)$alkyleneheterocyclyl;

$R^b$ is independently selected from: H, $(C_1\text{-}C_6)$alkyl, aryl, —$(C_1\text{-}C_6)$alkylenearyl, heterocyclyl, —$(C_1\text{-}C_6)$alkyleneheterocyclyl, $(C_3\text{-}C_6)$cycloalkyl, (C=O)$C_1\text{-}C_6$ alkyl, (C=O)$C_1\text{-}C_6$ alkyl or $S(O)_2R^a$; and $R^c$ is independently selected from: H, $(C_1\text{-}C_6)$alkyl, $(C_2\text{-}C_6)$alkenyl, $(C_3\text{-}C_6)$cycloalkyl, aryl, —$(C_1\text{-}C_6)$alkylenearyl, heterocyclyl and —$(C_1\text{-}C_6)$alkyleneheterocyclyl.

4. The compound according to claim 1 selected from:

8-phenyl-10H-furo[2',3':4,5]cyclohepta[1,2-b]pyridin-10-one;

8-chloro-10H-furo[2',3':4,5]cyclohepta[1,2-b]pyridin-10-one;

8-methoxy-10H-furo[2',3':4,5]cyclohepta[1,2-b]pyridin-10-one;

8-phenyl-10H-thieno[2',3':4,5]cyclohepta[1,2-b]pyridin-10-one;

6-phenyl-4H-thieno[3',2':4,5]cyclohepta[1,2-b]pyridin-4-one;

or a pharmaceutically acceptable salt thereof.

5. The compound according to claim 1 selected from:

8-phenyl-10H-furo[2',3':4,5]cyclohepta[1,2-b]pyridin-10-one;

8-phenyl-10H-thieno[2',3':4,5]cyclohepta[1,2-b]pyridin-10-one; and 6-phenyl-4H-thieno[3',':4,5]cyclohepta[1,2-b]pyridin-4-one.

6. A pharmaceutical composition that is comprised of a compound in accordance with claim 1 and a pharmaceutically acceptable carrier.

* * * * *